US010526415B2

(12) United States Patent
Liaudet-Coopman et al.

(10) Patent No.: US 10,526,415 B2
(45) Date of Patent: Jan. 7, 2020

(54) HUMAN MONOCLONAL ANTIBODIES FRAGMENTS INHIBITING BOTH THE CATH-D CATALYTIC ACTIVITY AND ITS BINDING TO THE LRP1 RECEPTOR

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); INSTITUT REGIONAL DU CANCER DE MONTPELLIER, Montpellier (FR)

(72) Inventors: Emmanuelle Liaudet-Coopman, Montpellier (FR); Thierry Chardes, Montpellier (FR); Pierre Martineau, Montpellier (FR); Yahya Ashraf, Montpellier (FR)

(73) Assignees: INSERM (INSTITUT NATIONAL DE LA SANTÉ ET DE LA RECHERCHE MÉDICALE), Paris (FR); UNIVERSITE DE MONTPELLIER, Montpellier (FR); INSTITUT REGIONAL DU CANCER DE MONTPELLIER, Montpellier (FR)

( * ) Notice: Subject to any disclaimer, the term of this patent is extended or adjusted under 35 U.S.C. 154(b) by 212 days.

(21) Appl. No.: 15/574,515

(22) PCT Filed: May 20, 2016

(86) PCT No.: PCT/EP2016/061454
§ 371 (c)(1),
(2) Date: Nov. 16, 2017

(87) PCT Pub. No.: WO2016/188911
PCT Pub. Date: Dec. 1, 2016

(65) Prior Publication Data
US 2018/0127510 A1 May 10, 2018

(30) Foreign Application Priority Data
May 22, 2015 (EP) ...................................... 15305775

(51) Int. Cl.
C07K 16/00 (2006.01)
C07K 16/30 (2006.01)
A61P 35/00 (2006.01)
C07K 16/40 (2006.01)
A61K 39/00 (2006.01)

(52) U.S. Cl.
CPC .......... *C07K 16/3015* (2013.01); *A61P 35/00* (2018.01); *C07K 16/40* (2013.01); *A61K 2039/505* (2013.01); *C07K 2317/21* (2013.01); *C07K 2317/76* (2013.01)

(58) Field of Classification Search
None
See application file for complete search history.

(56) References Cited

FOREIGN PATENT DOCUMENTS

EP 2045266 A1 4/2009
WO WO2009043858 * 4/2009

OTHER PUBLICATIONS

Murielle Glondu et al: "Down-regulation of cathepsin-D expression by antisense gene transfer inhibits tumor growth and experimental lung metastasis of human breast cancer cells", Oncogene, Jan. 1, 2002, pp. 5127-5134.
D Derocq et al: "Cathepsin D is partly endocytosed by the LRP1 receptor and inhibits LRP1-regulated intramembrane proteolysis", Oncogene, vol. 31, No. 26, Nov. 14, 2011, pp. 3202-3212.
Masson et al: "Pathophysiological functions of cathepsin D: Targeting its catalytic activity versus its protein binding activity?" Biochimie, Masson, Paris , FR, vol. 92, No. 11, Nov. 1, 2010, pp. 1635-1643.

* cited by examiner

*Primary Examiner* — Meera Natarajan
(74) *Attorney, Agent, or Firm* — W&C IP

(57) ABSTRACT

The invention relates to human anti-Cath-D neutralizing monoclonal antibodies and uses thereof. More particularly, the invention relates to an isolated human monoclonal antibody or a fragment thereof comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region. The invention also relates to an isolated human monoclonal antibody or a fragment thereof comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region.

16 Claims, 10 Drawing Sheets
Specification includes a Sequence Listing.

Figure 1C:
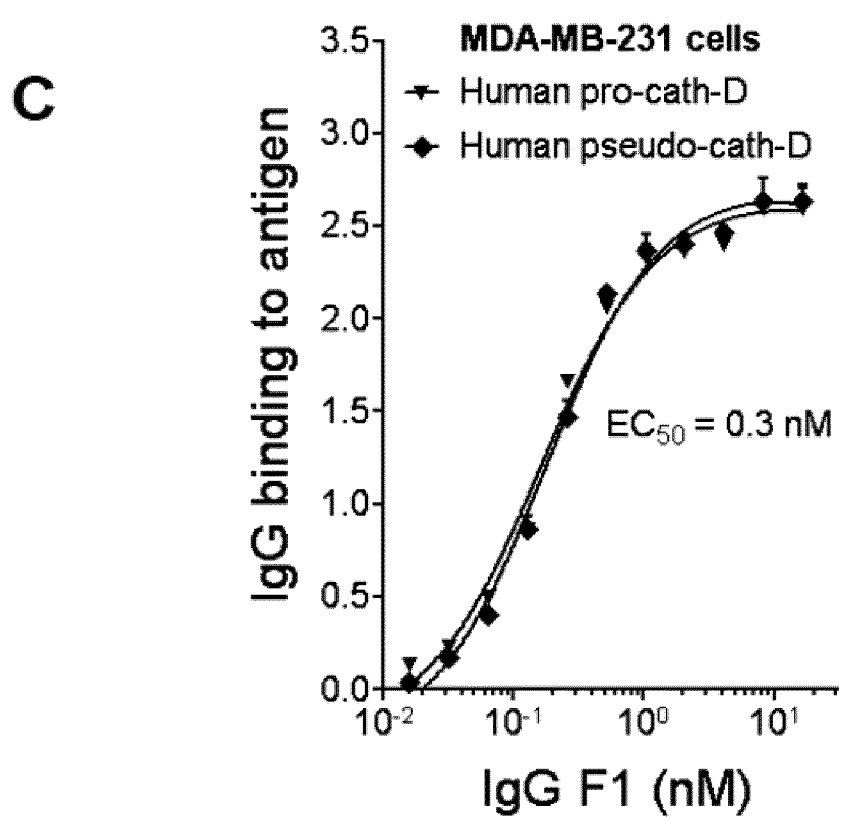

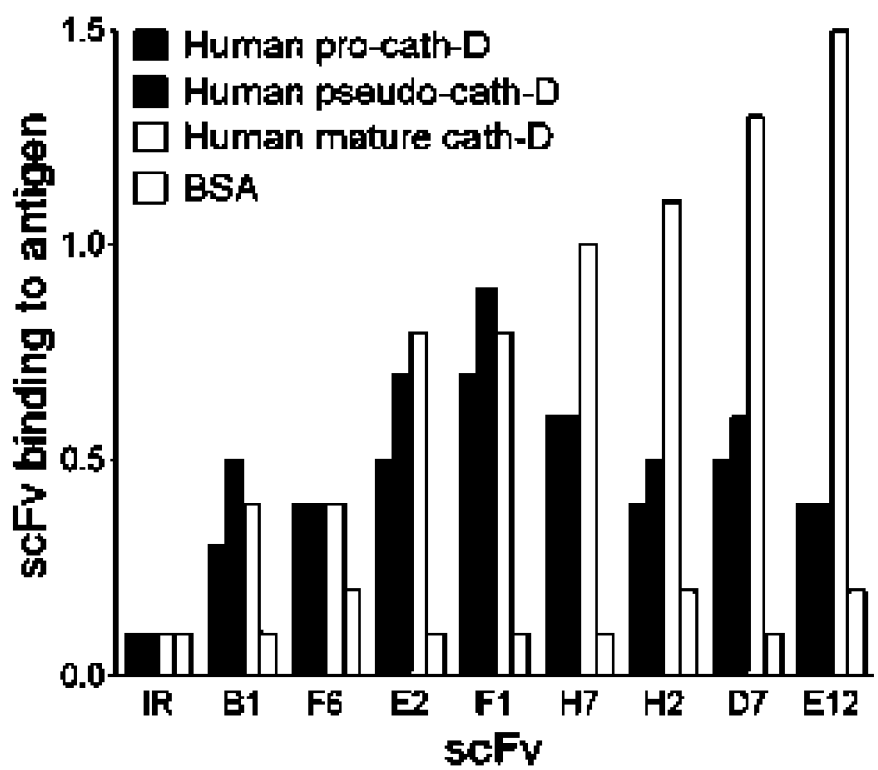
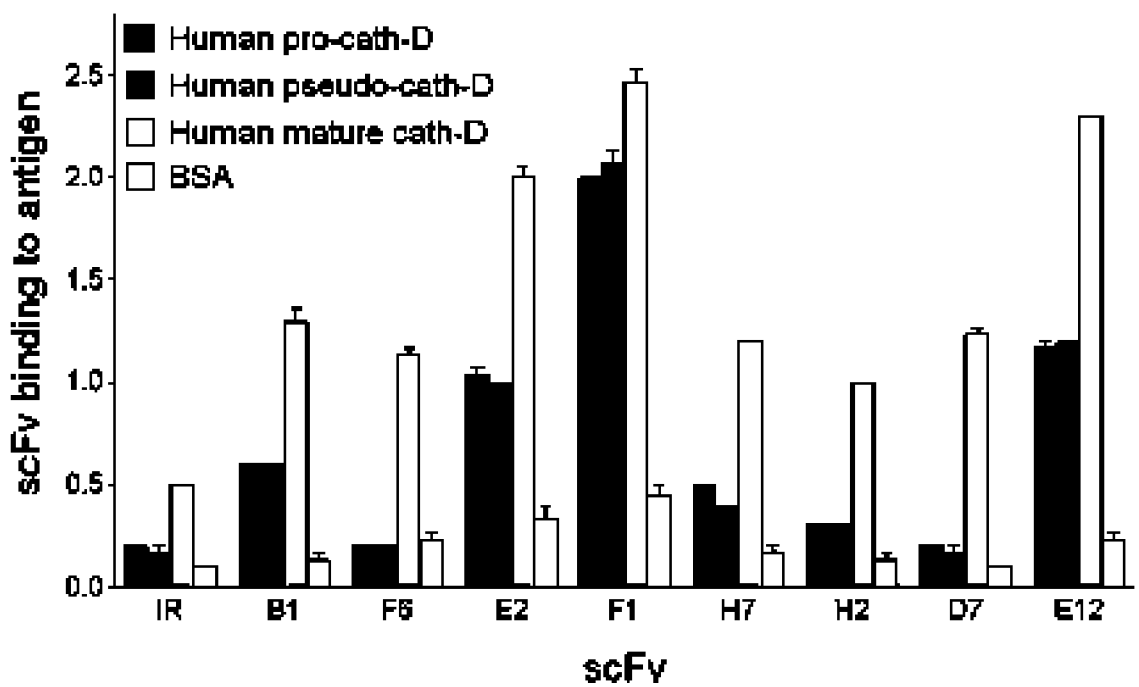
Figures 1A&B

C

| scFv | Ki ± SD (nM) |
|---|---|
| B1 | N.D |
| F6 | 326 ± 80 |
| E2 | 754 ± 37 |
| F1 | 212 ± 86 |
| H7 | 675 ± 18 |
| H2 | N.D |
| D7 | N.D |
| E12 | 574 ± 90 |

Figure 3

| scFv | Ki ± SD (nM) |
|---|---|
| B1 | 19 ± 6.3 |
| F6 | N.D |
| E2 | 24 ± 7.4 |
| F1 | 100 ± 29 |
| H7 | 400 ± 89 |
| H2 | 100 ± 34 |
| D7 | N.D |
| E12 | 2.2 ± 0.8 |

Figure 4

A

SEQUENCE LISTING

<160> NUMBER OF SEQ ID NOS: 20

<210> SEQ ID NO 1
<211> LENGTH: 120
<212> TYPE: PRT
<213> ORGANISM: Artificial
<220> FEATURE:
<223> OTHER INFORMATION: Synthetic E2 VH chain

<400> SEQUENCE: 1

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Ser
            20                  25                  30

Tyr Met Asn Trp Val Arg Gln Ala Pro Gly Lys Gly Leu Glu Trp Ile
        35                  40                  45

```
Ser Tyr Ile Ser Gly Ser Ser Arg Tyr Ser Tyr Ala Asp Phe Val Lys
        50                  55                  60
Gly Arg Phe Thr Ile Ser Arg Asp Asn Ala Thr Asn Ser Leu Tyr Leu
 65                  70                  75                  80
Gln Met Asn Ser Leu Arg Ala Glu Asp Thr Ala Val Tyr Tyr Cys Val
                 85                  90                  95
Arg Ser Ser Asn Ser Tyr Phe Gly Gly Gly Met Asp Val Trp Gly Arg
            100                 105                 110
Gly Thr Leu Val Thr Val Ser Ser
        115                 120

<210> SEQ ID NO 2
<211> LENGTH: 8
<212> TYPE: PRT
<213> ORGANISM: Artificial
<220> FEATURE:
<223> OTHER INFORMATION: Synthetic E2 H-CDR1

<400> SEQUENCE: 2

Gly Phe Thr Phe Ser Asn Ser Tyr
1               5

<210> SEQ ID NO 3
<211> LENGTH: 8
<212> TYPE: PRT
<213> ORGANISM: Artificial
<220> FEATURE:
<223> OTHER INFORMATION: Synthetic E2 H-CDR2

<400> SEQUENCE: 3

Ile Ser Gly Ser Ser Arg Tyr Ile
1               5

<210> SEQ ID NO 4
<211> LENGTH: 14
<212> TYPE: PRT
<213> ORGANISM: Artificial
<220> FEATURE:
<223> OTHER INFORMATION: Synthetic E2 H-CDR3

<400> SEQUENCE: 4

Val Arg Ser Ser Asn Ser Tyr Phe Gly Gly Gly Met Asp Val
1               5                   10

<210> SEQ ID NO 5
<211> LENGTH: 110
<212> TYPE: PRT
<213> ORGANISM: Artificial
<220> FEATURE:
<223> OTHER INFORMATION: Synthetic E2 VL chain

<400> SEQUENCE: 5

Gln Ser Val Leu Thr Gln Pro Ala Ser Val Ser Gly Ser Pro Gly Gln
1               5                   10                  15
Ser Ile Thr Ile Ser Cys Ala Gly Thr Ser Ser Asp Val Gly Gly Ser
            20                  25                  30
Tyr Gly Val Ser Trp Tyr Gln Gln His Pro Gly Lys Ala Pro Lys Leu
        35                  40                  45
Met Ile Tyr Gly Asp Ser Tyr Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Thr Asn Tyr
                85                  90                  95

Ser Thr Arg Val Phe Gly Gly Gly Thr Lys Leu Ala Val Leu
            100                 105                 110

<210> SEQ ID NO 6
<211> LENGTH: 9
<212> TYPE: PRT
<213> ORGANISM: Artificial
<220> FEATURE:
<223> OTHER INFORMATION: Synthetic E2 L-CDR1

<400> SEQUENCE: 6

Ser Ser Asp Val Gly Gly Ser Tyr Gly
1               5

<210> SEQ ID NO 7
<211> LENGTH: 3
<212> TYPE: PRT
<213> ORGANISM: Artificial
<220> FEATURE:
<223> OTHER INFORMATION: Synthetic E2 L-CDR2

<400> SEQUENCE: 7

Gly Asp Ser
1

<210> SEQ ID NO 8
<211> LENGTH: 10
<212> TYPE: PRT
<213> ORGANISM: Artificial
<220> FEATURE:
<223> OTHER INFORMATION: Synthetic E2 L-CDR3

<400> SEQUENCE: 8

Ser Ser Tyr Thr Asn Tyr Ser Thr Arg Val
1               5                   10

<210> SEQ ID NO 9
<211> LENGTH: 117
<212> TYPE: PRT
<213> ORGANISM: Artificial
<220> FEATURE:
<223> OTHER INFORMATION: Synthetic F1 VH chain

<400> SEQUENCE: 9

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Ser Asn Asn Tyr
            20                  25                  30

Met Asn Trp Val Arg Gln Ala Pro Gly Lys Gly Leu Glu Trp Ile Ser
        35                  40                  45

Tyr Ile Ser Gly Ser Ser Arg Tyr Ile Ser Tyr Ala Asp Phe Val Lys
    50                  55                  60

Gly Arg Phe Thr Ile Ser Arg Asp Asn Ala Thr Asn Ser Leu Tyr Leu
65                  70                  75                  80

Gln Met Asn Ser Leu Arg Ala Glu Asp Thr Ala Val Tyr Tyr Cys Val
                85                  90                  95

Arg Ser Ser Asn Ser Gly Gly Met Asp Val Trp Gly Arg Gly Thr Leu
            100                 105                 110

Val Thr Val Ser Ser
            115
```

<210> SEQ ID NO 10
<211> LENGTH: 8
<212> TYPE: PRT
<213> ORGANISM: Artificial
<220> FEATURE:
<223> OTHER INFORMATION: Synthetic F1 H-CDR1

<400> SEQUENCE: 10

Gly Phe Thr Phe Ser Asn Asn Tyr
1               5

<210> SEQ ID NO 11
<211> LENGTH: 8
<212> TYPE: PRT
<213> ORGANISM: Artificial
<220> FEATURE:
<223> OTHER INFORMATION: Synthetic F1 H-CDR2

<400> SEQUENCE: 11

Ile Ser Gly Ser Ser Arg Tyr Ile
1               5

<210> SEQ ID NO 12
<211> LENGTH: 11
<212> TYPE: PRT
<213> ORGANISM: Artificial
<220> FEATURE:
<223> OTHER INFORMATION: Synthetic F1 H-CDR3

<400> SEQUENCE: 12

Val Arg Ser Ser Asn Ser Gly Gly Met Asp Val
1               5                   10

<210> SEQ ID NO 13
<211> LENGTH: 110
<212> TYPE: PRT
<213> ORGANISM: Artificial
<220> FEATURE:
<223> OTHER INFORMATION: Synthetic F1 VL chain

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Tyr Gly Val Ser Trp Tyr Gln Gln His Pro Gly Lys Ala Pro Lys Leu
        35                  40                  45

Met Ile Tyr Tyr Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Asn
                85                  90                  95

Ser Thr Arg Val Phe Gly Gly Gly Thr Lys Leu Ala Val Leu
            100                 105                 110

<210> SEQ ID NO 14
<211> LENGTH: 9
<212> TYPE: PRT
<213> ORGANISM: Artificial
<220> FEATURE:
<223> OTHER INFORMATION: Synthetic F1 L-CDR1

<400> SEQUENCE: 14

```
Ser Ser Asp Val Gly Gly Tyr Tyr Gly
1               5

<210> SEQ ID NO 15
<211> LENGTH: 3
<212> TYPE: PRT
<213> ORGANISM: Artificial
<220> FEATURE:
<223> OTHER INFORMATION: Synthetic F1 L-CDR2

<400> SEQUENCE: 15

Tyr Asp Ser
1

<210> SEQ ID NO 16
<211> LENGTH: 10
<212> TYPE: PRT
<213> ORGANISM: Artificial
<220> FEATURE:
<223> OTHER INFORMATION: Synthetic F1 L-CDR3

<400> SEQUENCE: 16

Ser Ser Tyr Thr Ser Asn Ser Thr Arg Val
1               5                   10

<210> SEQ ID NO 17
<211> LENGTH: 6
<212> TYPE: PRT
<213> ORGANISM: Artificial
<220> FEATURE:
<223> OTHER INFORMATION: Synthetic Epitope 1 (Peptide ranging from amino
      acids 128-134 of human Cath-D)

<400> SEQUENCE: 17

Ala Ala Lys Phe Asp Gly
1               5

<210> SEQ ID NO 18
<211> LENGTH: 8
<212> TYPE: PRT
<213> ORGANISM: Artificial
<220> FEATURE:
<223> OTHER INFORMATION: Synthetic Epitope 2 (Peptide ranging from amino
      acids 172-179 of human Cath-D)

<400> SEQUENCE: 18

Asp Pro Asp Ala Gln Pro Gly Gly
1               5

<210> SEQ ID NO 19
<211> LENGTH: 10
<212> TYPE: PRT
<213> ORGANISM: Artificial
<220> FEATURE:
<223> OTHER INFORMATION: Synthetic Epitope 3 (Peptide ranging from amino
      acids 188-197 of human Cath-D)

<400> SEQUENCE: 19

Lys Val Ser Gln Ala Gly Lys Thr Leu Cys
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic Epitope 4 (peptide ranging from amino
``` acids 220-228 of human Cath-D)

<400> SEQUENCE: 20

Thr Leu Cys Lys Glu Gly Cys Glu Ala
1               5

HUMAN MONOCLONAL ANTIBODIES FRAGMENTS INHIBITING BOTH THE CATH-D CATALYTIC ACTIVITY AND ITS BINDING TO THE LRP1 RECEPTOR

FIELD OF THE INVENTION

The invention relates to human anti-Cath-D neutralizing monoclonal antibodies and uses thereof. More particularly, the invention relates to human monoclonal antibodies fragments inhibiting both the Cath-D catalytic activity and its binding to the LRP1 (LDL receptor-related protein-1) receptor.

BACKGROUND OF THE INVENTION

Breast Cancer is one of the leading causes of death in women in the developed world [1]. High incidence triple-negative breast cancers (ER− and PR−, HER2-non amplified) present unsatisfactory treatments. In addition, ER+ breast cancers also became resistant to hormone-therapy. Thus novel treatments for breast cancer are urgently needed. Tumor progression has been recognized as the product of evolving cross-talk between tumor cells and the surrounding supportive tissue, known as the tumor stroma [2]. Cancer cells interact dynamically with several normal cell types within the extra-cellular matrix, such as fibroblasts, infiltrating immune cells, endothelial cells and adipocytes. Stromal and tumor cells exchange enzymes, growth factors and cytokines that modify the local extracellular matrix, stimulate migration and invasion, and promote the proliferation and survival of stromal and tumor cells. In the last decade, it has become increasingly evident that tumor cells create a peri-cellular microenvironment where molecules such as metalloproteinases, serine proteases, cysteine and aspartic cathepsins interact to form a pro-tumorigenic proteolytic network [3]. Extracellular proteases are thus primary targets for drug discovery because of their differential expression in cancer [4-6]

The lysosomal aspartic protease cathepsin D (Cath-D) is one of the most abundant lysosomal endo-proteinases implicated in protein catabolism. Human Cath-D is synthesized as a 52-kDa precursor that is converted to an active 48-kDa single-chain intermediate within the endosomes, and then to the fully active mature protease, that consists of a 34-kDa heavy chain and a 14-kDa light chain, in the lysosomes. Cath-D catalytic site has two critical aspartate residues (amino acids 33 and 231). Cath-D requires an acidic pH to be proteolytically active. Cath-D is massively overproduced and secreted by many solid tumors solid tumors: breast cancer, melanoma, ovarian cancer, lung cancer, liver cancer, pancreatic cancer, endometrial cancer, head and neck cancer, bladder cancer, malignant glioma [7]. Cath-D is a well-established independent marker of poor prognosis for breast cancer associated with metastasis [8, 9]. Several groups have shown that Cath-D affects both the cancer and stromal cell behaviors. The inhibition of Cath-D expression in breast cancer cells (BCC) decreases tumor growth and metastasis [10, 11]. Human pro-Cath-D cDNA transfected in cancer cells promotes cancer cell proliferation, tumor growth and angiogenesis, and metastasis [12-15]. $^{Cath-D-/-}$MEF fibroblasts transfected with human pro-Cath-D cDNA produce more outgrowth in three-dimensional matrices [16]. We and others have shown that the overproduction of Cath-D by breast cancer cells leads to the autocrine specific hypersecretion of the 52-kDa pro-Cath-D into the extracellular environment [17, 18]. Pro-Cath-D is also secreted by macrophages infiltrating inflammatory tumors and by endothelial cells in response to inflammatory cytokines [19, 20]. Secreted human pro-Cath-D stimulates BCC proliferation [17, 18], fibroblast outgrowth [16], and endothelial cell growth [21]. Purified 52-kDa pro-Cath-D undergoes acid-dependent auto-activation in vitro, to form a catalytically-active 51-kDa pseudo-Cath-D, that retains 18 residues (27-44) of the pro-segment [22]. Since the extracellular microenvironment of hypoxic and inflammatory tumors is acidic due to the production of excess cellular acids [23-25], secreted 52 kDa pro-cath-D may auto-activate locally into proteolytically-active 51-kDa pseudo-Cath-D. At the low pH (6.8-5.5) found in tumors, Cath-D secreted by BCC degrades cystatin C, one of the most potent extracellular inhibitor of cysteine cathepsins [26]. This in turn enhances cysteine cathepsin proteolytic activity, revealing a new link in the protease web [27]. In addition, secreted Cath-D also affects BCC and stromal cells of the tumor microenvironment independently of its catalytic activity [13, 16]. Vetvicka's group described that Cath-D autocrine mitogenic growth factor activity on BCC is mediated by its activation peptide localized in a nine amino acid stretch (aa 36-44) within the Cath-D pro-peptide interacting with an unknown cell surface receptor [28]. Secreted also Cath-D promotes mammary fibroblast outgrowth via binding to LRP1 receptor (LDL receptor-related protein-1) [29, 30]. Collectively these findings provide good evidences of the oncogenic role of secreted pro-Cath-D by both proteolytic and non-proteolytic molecular mechanisms. Moreover, anti-Cath-D auto-antibodies [31] have been detected in the early stages of breast, melanoma, ovarian and lung cancers [32-35], indicating that Cath-D can be considered as a tumor-associated antigen (TAA).

Targeting Cath-D released in the tumor microenvironment will require the use of inhibitors of its catalytic activity but also the development of new tools inhibiting its interacting functions. The antibody-based delivery of therapeutic agents to the tumor site is an emerging field of modern anti-cancer research, which promises to concentrate bioactive molecules onto neoplastic lesions while sparing normal tissues. Originally monoclonal antibodies specific to membrane antigens on cancer cells have been used for tumor targeting applications. Alternative targets such as antibody-based targeting of proteases, which are hypersecreted in the tumor microenvironment, represent an additional attractive avenue for pharmaco-delivery applications [36].

New treatments are required for triple-negative (ER− and PR−, HER2-non amplified) and hormono-resistant breast cancers. The aspartic protease cathepsin D (Cath-D), an independent marker of poor prognosis in breast cancer, is over-expressed and hyper-secreted within the breast tumor micro-environment. Secreted Cath-D can affect the breast tumor microenvironment by degrading cystatin C, the most potent cysteine cathepsin inhibitor, and by triggering mammary fibroblast outgrowth via the LDL receptor-related protein-1, LRP1. Targeting secreted Cath-D in breast cancer thus requires the use of inhibitors of its catalytic activity and of its interacting functions.

SUMMARY OF THE INVENTION

In a first aspect, the invention relates to an isolated human monoclonal antibody or a fragment thereof inhibiting both the Cath-D catalytic activity and its binding to the LRP1 receptor.

In a second aspect, the invention relates to an isolated human monoclonal antibody or a fragment thereof comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region.

In a third aspect, the invention relates to an isolated human monoclonal antibody or a fragment thereof comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region.

In a fourth aspect, the invention relates to an antibody or a fragment thereof according to the invention for use as a drug.

In a fifth aspect, the invention relates to an isolated human anti-Cath-D monoclonal antibody or a fragment thereof for use in a method for treating breast cancer.

DETAILED DESCRIPTION OF THE INVENTION

The inventors described the isolation and characterization of human monoclonal antibody scFv fragments specific to Cath-D by phage display. The Cath-D-binder scFv were functionally screened for their ability to inhibit both the proteolytic activity of Cath-D and its binding to the fibroblastic LRP1 receptor. Two scFv cloned under IgG1, λ format (anti-Cath-D IgG1 F1 and E2) inhibited triple-negative and ER+ breast cancer cell wound healing, colony formation and three-dimensional outgrowth in Matrigel. Anti-Cath-D IgG1 F1 and E2 significantly reduced tumor growth of triple-negative MDA-MB-231 breast cancer cells in nude mice. These findings strongly suggest that antibody-based targeting of Cath-D within the breast tumor microenvironment may have therapeutic efficacy for breast cancer treatment.

Definitions

Throughout the specification, several terms are employed and are defined in the following paragraphs.

The term "Cath-D" has its general meaning in the art and refers to lysosomal aspartic protease cathepsin-D. Cath-D is synthesized as the 52 kDa, catalytically inactive, precursor called pro-Cath-D. It is present in endosomes as an active 48 kDa single-chain intermediate that is subsequently converted in the lysosomes into the fully active mature protease, composed of a 34 kDa heavy and a 14 kDa light chains. The naturally occurring pro-cath-D protein has an amino acid sequence shown in Genbank, Accession number NP_001900.

The term "anti-Cath-D antibody" refers to an antibody directed against Cath-D.

According to the invention, the terms "antibody" or "immunoglobulin" have the same meaning, and will be used equally in the invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG (encompassing distinct subclasses such as IgG1, IgG2, IgG3 and IgG4), IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

As used herein, the term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

As used herein, the term "Fab'" refers to an antibody fragment having a molecular weight of about 50,000 and antigen binding activity, which is obtained by cutting a disulfide bond of the hinge region of the F(ab')2.

As used herein, the term "single chain Fv" ("scFv") polypeptide is a covalently linked VH::VL heterodimer which is usually expressed from a gene fusion including VH and VL encoding genes linked by a peptide-encoding linker.

As used herein, the term "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

As used herein, the term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein, the terms "neutralizing antibody" refers to an antibody that blocks or reduces at least one activity of a polypeptide comprising the epitope to which the antibody specifically binds. A neutralizing antibody reduces Cathepsin D biological activity in in cellulo and/or in vivo tests. Typically, an anti-Cath-D neutralizing antibody fragment blocks Cath-D binding to LRP1 (which can be assessed by GST pull-down assays) and/or also inhibits catalytic activity of mature Cath-D (which can be assessed by a catalytic activity assay based on the cleavage reaction by Cath-D of a fluorogenic substrate such as M2295 (fluorogenic peptide substrate for pseudo-Cath-D) or M0938 (fluorogenic peptide substrate for mature Cath-D) as described below.

The term "LRP1" has its general meaning in the art (Strickland and Ranganathan, 2003; Lillis et al., 2005) and refers to LDL receptor-related protein 1. LRP1 is composed of a 515 kDa extracellular a chain and an 85 kDa β chain generated by proteolytic cleavage from a 600 kDa precursor polypeptide in a trans-Golgi compartment. Actually, LRP1α chain and LRP1β chain are issued from a sole transcript. By way of example, the human full length of unprocessed precursor LRP1 corresponds to SwissProt accession number Q07954.

By "purified" and "isolated" it is meant, when referring to an antibody according to the invention, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present.

Antibodies of the Invention:

The invention provides for isolated anti-Cath-D neutralizing monoclonal antibodies or fragments thereof.

In a first aspect, the invention thus relates to an isolated human monoclonal antibody or a fragment thereof inhibiting both the Cath-D catalytic activity and its binding to the LRP1 receptor.

In one embodiment, said antibody specifically binds to the peptide of SEQ ID NO: 17 derived from 34-kDa Cath-D (peptide ranging from amino acids 128-134 of Cath-D) as follows: $^{128}$AAKFDG$^{134}$.

In one embodiment, said antibody specifically binds to the peptide of SEQ ID NO: 18 derived from 34-kDa Cath-D (peptide ranging from amino acids 172-179 of Cath-D) as follows: $^{172}$DPDAQPGG$^{179}$.

In one embodiment, said antibody specifically binds to the peptide of SEQ ID NO: 19 derived from 34-kDa Cath-D (peptide ranging from amino acids 293-302 of Cath-D) as follows: $^{293}$KVSQAGKTLC$^{302}$.

In one embodiment, said antibody specifically binds to the peptide of SEQ ID NO: 20 derived from 34-kDa Cath-D (peptide ranging from amino acids 220-228 of Cath-D) as follows: $^{220}$TLCKEGCEA$^{228}$.

In particular, the inventors have isolated by antibody phage display two fully human anti-Cath-D single-chain variable antibody fragment (scFv), selected on human 51-kDa pseudo-cath D and human cellular mature (34+14-kDa) Cath-D, referred as E2 and F1.

The inventors have cloned and characterized the variable domain of the light and heavy chains of said scFv E2, and thus determined the complementary determining regions (CDRs) domain of said antibody as described in Table 1:

| ScFv E2 Domains | Sequence (defined by IMGT unique numbering for IgG) [73] |
|---|---|
| VH | EVQLVESGGSLVKPGGSLRLSCAASGFTFSNSYMNWVRQAP GKGLEWISYISGSSRYSYADFVKGRFTISRDNATNSLYLQM NSLRAEDTAVYYCVRSSNSYFGGGMDVWGRGTLVTVSS (SEQ ID NO: 1) |
| H-CDR1 | GFTFSNSY (SEQ ID NO: 2) |
| H-CDR2 | ISGSSRYI (SEQ ID NO: 3) |
| H-CDR3 | VRSSNSYFGGGMDV (SEQ ID NO: 4) |
| VL | QSVLTQPASVSGSPGQSITISCAGTSSDVGGSYGVSWYQQH PGKAPKLMIYGDSYRPSGVSNRFSGSKSGNTASLTISGLQA EDEADYYCSSYTNYSTRVFGGGTKLAVL (SEQ ID NO: 5) |
| L-CDR1 | SSDVGGSYG (SEQ ID NO: 6) |
| L-CDR2 | GDS (SEQ ID NO: 7) |
| L-CDR3 | SSYTNYSTRV (SEQ ID NO: 8) |

Therefore, the invention relates to an antibody having specificity for Cath-D, comprising a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3.

The invention also relates to an antibody having specificity for Cath-D, comprising a light chain wherein the variable domain comprises at least one CDR having a sequence selected from the group consisting of SEQ ID NO: 6 for L-CDR1, SEQ ID NO: 7 for L-CDR2 and SEQ ID NO: 8 for L-CDR3.

The antibody of the invention, may comprise a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3 and a light chain wherein the variable domain comprises at least one CDR having a sequence selected from the group consisting of SEQ ID NO: 6 for L-CDR1, SEQ ID NO: 7 for L-CDR2 and SEQ ID NO: 8 for L-CDR3.

In particular, the invention provides an anti-Cath-D antibody comprising:

an heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region.

In a particular embodiment, the heavy chain variable region of said antibody has the amino acid sequence set forth as SEQ ID NO: 1 and/or the light chain variable region has the amino acid sequence set forth as SEQ ID NO: 5.

The inventors also have cloned and characterized the variable domain of the light and heavy chains of said scFv F1, and thus determined the complementary determining regions (CDRs) domain of said antibody as described in Table 2:

| ScFv F1 Domains | Sequence (defined by IMGT unique numbering for IgG)1731 |
|---|---|
| VH | EVQLVESGGSLVKPGGSLRLSCAASGFTSNNYMNWVRQAP GKGLEWISYISGSSRYISYADFVKGRFTISRDNATNSLYL QMNSLRAEDTAVYYCVRSSNSGGMDVWGRGTLVTVSS (SEQ ID NO: 9) |
| H-CDR1 | GFTFSNNY (SEQ ID NO: 10) |
| H-CDR2 | ISGSSRYI (SEQ ID NO: 11) |
| H-CDR3 | VRSSNSGGMDV (SEQ ID NO: 12) |
| VL | QSVLTQPASVSGSPGQSITISCAGTSSDVGGYYGVSWYQQH PGKAPKLMIYYDSYRPSGVSNRFSGSKSGNTASLTISGLQA EDEADYYCSSYTSNSTRVFGGGTKLAVL (SEQ ID NO: 13) |
| L-CDR1 | SSDVGGYYG (SEQ ID NO: 14) |
| L-CDR2 | YDS (SEQ ID NO: 15) |
| L-CDR3 | SSYTSNSTRV (SEQ ID NO: 16) |

Therefore, the invention relates to an antibody having specificity for Cath-D, comprising a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3.

The invention also relates to an antibody having specificity for Cath-D, comprising a light chain wherein the variable domain comprises at least one CDR having a sequence selected from the group consisting of SEQ ID NO: 14 for L-CDR1, SEQ ID NO: 15 for L-CDR2 and SEQ ID NO: 16 for L-CDR3.

The antibody of the invention, may comprise a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3 and a light chain wherein the variable domain comprises at least one CDR having a sequence selected from the group consisting of SEQ ID NO: 14 for L-CDR1, SEQ ID NO: 15 for L-CDR2 and SEQ ID NO: 16 for L-CDR3.

In particular, the invention provides an anti-Cath-D antibody comprising:
an heavy chain variable region comprising SEQ ID NO: 10 in the H-CDR1 region, SEQ ID NO: 11 in the H-CDR2 region and SEQ ID NO: 12 in the H-CDR3 region; and
a light chain variable region comprising SEQ ID NO: 14 in the L-CDR1 region, SEQ ID NO: 15 in the L-CDR2 region and SEQ ID NO: 16 in the L-CDR3 region.

In a particular embodiment, the heavy chain variable region of said antibody has the amino acid sequence set forth as SEQ ID NO: 9 and/or the light chain variable region has the amino acid sequence set forth as SEQ ID NO: 13 The invention further provides fragments of said antibodies directed against Cath-D which include but are not limited to Fv, Fab, F(ab')2, Fab', dsFv, scFv, sc(Fv)2 and diabodies.

It should be also noted that the antibodies F1 and E2 cross-react with murin Cath-D, which is of interest for preclinical evaluation and toxicological studies.

It should be further noted that the E2 and F1 antibodies (e.g. with the IgG1 isotype) specifically bind to cathepsin D, and do not bind with others aspartic proteases (e.g. cathepsin E, pepsinogen A and pepsinogen C).

In another aspect, the invention relates to a polypeptide which has a sequence selected from the group consisting of SEQ ID NO: 1, SEQ ID NO: 2, SEQ ID NO: 3, SEQ ID NO: 4, SEQ ID NO: 5; SEQ ID NO: 6; SEQ ID NO: 7; SEQ ID NO: 8; SEQ ID NO: 9; SEQ ID NO: 10, SEQ ID NO: 11, SEQ ID NO: 12, SEQ ID NO: 13; SEQ ID NO: 14; SEQ ID NO: 15 and SEQ ID NO: 16.

In another aspect, the invention provides a monoclonal antibody that competes for binding to 34-kDa Cath-D with the anti-Cath-D IgG1 F1 and E2 as defined above.

In a particular embodiment, the invention provides a monoclonal antibody that competes for binding to peptides of SEQ ID NO: 17, SEQ ID NO: 18, SEQ ID NO: 19, or SEQ ID NO: 20 with the anti-Cath-D IgG (in particular IgG1) F1 and E2 as defined above.

Competitive Binding Assays:

The invention thus relates to an isolated monoclonal antibody scFc fragment that; competes for binding to Cath-D with the anti-Cath-D IgG (in particular IgG1) F1 and E2 of the invention as defined above and inhibits both the Cath-D catalytic activity and its binding to the LRP1 fibroblastic receptor.

In a particular embodiment, the invention provides-s a monoclonal antibody that may competes for binding to peptides of SEQ ID NO: 17, SEQ ID NO: 18, SEQ ID NO: 19, or SEQ ID NO: 20 with the anti-Cath-D IgG (in particular IgG1) F1 and E2 as defined above.

Epitope binning can be used to identify antibodies that fall within the scope of the claimed invention. Epitope binning refers to the use of competitive binding assays to identity pairs of antibodies that are, or are not, capable of binding Cath-D simultaneously, thereby identifying pairs of antibodies that bind to the same or overlapping epitopes on Cath-D. Epitope binning experiments provide evidence that antigenically distinct epitopes are present. Competition for binding can be evaluated for any pair of antibodies or fragments. For example, using the appropriate detection reagents, the binding specificity of antibodies or binding fragments from any source can be compared to the binding specificity of the monoclonal antibodies disclosed herein. Epitope binning can be performed with "isolated antibodies" or with cell culture supernatants. Frequently, binning is performed with first round clonal supernatants to guide the choice of clones to be developed further. The antibodies to be compared should be substantially homogeneous antigen binding domains. In the case of "bispecific" or "bifunctional" antibodies the binding specificity of the two different binding sites need to be evaluated or binned independently.

The antibodies of the invention may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope binning panels of monoclonal antibodies. Additionally, routine cross-blocking assays such as those described in Antibodies, A Laboratory Manual, Cold Spring Harbor Laboratory, Ed Harlow and David Lane, 1988, can be performed.

Methods of Producing Antibodies of the Invention:

Anti-Cath-D antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further aspect of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene ("DHFR gene") is defective (Urlaub G et al; 1980), rat YB2/3HL.P2.G11.16Ag.20 cell (ATCC CRL1662, hereinafter referred to as "YB2/0 cell"), and the like.

The invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Antibodies of the invention are suitably separated from the culture medium by conventional immunoglobulin purification procedures such as protein A-Sepharose, hydroxylapatite chromatography, gel electrophoresis, dialysis, or affinity chromatography.

Amino acid sequence modification(s) of the antibodies described herein are contemplated. For example, it may be desirable to improve the binding affinity and/or other biological properties of the antibody. Modifications and changes may be made in the structure of the antibodies of the invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, antibodies of the invention may be affinity matured antibodies.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology, 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene, 1 69:147-155 (1995); Yelton et al. J. Immunol., 155:1994-2004 (1995); Jackson et al., J. Immunol., 154(7):3310-9 (1995); and Hawkins et al, J. Mol. Biol., 226:889-896 (1992).

A further aspect of the invention also encompasses function-conservative variants of the antibodies of the invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Accordingly, the invention also provides an antibody comprising a heavy chain wherein the variable domain comprises:
  a H-CDR1 having at least 90% or 95% identity with sequence set forth as SEQ ID NO: 2,
  a H-CDR2 having at least 90% or 95% identity with sequence set forth as SEQ ID NO: 3,
  a H-CDR3 having at least 90% or 95% identity with sequence set forth as SEQ ID NO: 4,
  a L-CDR1 having at least 90% or 95% identity with sequence set forth as SEQ ID NO: 6,
  a L-CDR2 having at least 90% or 95% identity with sequence set forth as SEQ ID NO: 7,
  a L-CDR3 having at least 90% or 95% identity with sequence set forth as SEQ ID NO: 8, and
  that specifically binds to Cath-D with substantially the same affinity as an antibody comprising a heavy chain wherein the variable domain comprises SEQ ID NO: 2 for H-CDR1, SEQ ID NO: 3 for H-CDR2 and SEQ ID NO: 4 for H-CDR3 and a light chain wherein the variable domain comprises SEQ ID NO: 6 for L-CDR1, SEQ ID NO: 7 for L-CDR2 and SEQ ID NO: 8 for L-CDR3, and more preferably with substantially the same affinity as the the bivalent scFv-Fc E2.

The invention further provides an antibody comprising a heavy chain wherein the variable domain comprises:
  a H-CDR1 having at least 90% or 95% identity with sequence set forth as SEQ ID NO: 10,
  a H-CDR2 having at least 90% or 95% identity with sequence set forth as SEQ ID NO: 11,
  a H-CDR3 having at least 90% or 95% identity with sequence set forth as SEQ ID NO: 12,
  a L-CDR1 having at least 90% or 95% identity with sequence set forth as SEQ ID NO: 14,
  a L-CDR2 having at least 90% or 95% identity with sequence set forth as SEQ ID NO: 15,
  a L-CDR3 having at least 90% or 95% identity with sequence set forth as SEQ ID NO: 16, and
  that specifically binds to Cath-D with substantially the same affinity as an antibody comprising a heavy chain wherein the variable domain comprises SEQ ID NO: 10 for H-CDR1, SEQ ID NO: 11 for H-CDR2 and SEQ ID NO: 12 for H-CDR3 and a light chain wherein the variable domain comprises SEQ ID NO: 14 for L-CDR1, SEQ ID NO: 15 for L-CDR2 and SEQ ID NO: 16 for L-CDR3, and more preferably with substantially the same affinity as the bivalent scFv-Fc F1.

Said antibodies may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich"

immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al., 2001 J. Biol. Chen. 276:6591-6604, WO2010106180).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery.

Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html).

Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP0154316 by Nishimura et al. and EP0401384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094. Another possibility is a fusion of at least the antigen-binding region of the antibody of the invention to proteins capable of binding to serum proteins, such human serum albumin to increase half-life of the resulting molecule. Such approach is for example described in Nygren et al., EP 0 486 525.

Immunoconjugates:

An antibody of the invention can be conjugated with a detectable label to form an anti-Cath-D immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-Cath-D immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Cath-D immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Cath-D immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Cath-D immunoconjugates can be detectably labeled by linking an anti-Cath-D antibody to an enzyme. When the anti-Cath-D-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-Cath-D monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-Cath-D monoclonal antibodies that have been conjugated with avidin, streptavidin, and biotin. (See, e.g., Wilchek et al. (eds.), "Avidin-Biotin Technology," *Methods In Enzymology (Vol. 184)* (Academic Press 1990); Bayer et al., "Immunochemical Applications of Avidin-Biotin Technology," in *Methods In Molecular Biology* (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

In another aspect, the invention provides an anti-Cath-D antibody-drug conjugate. An "anti-Cath-D antibody-drug conjugate" as used herein refers to an anti-Cath-D antibody according to the invention conjugated to a therapeutic agent. Such anti-Cath-D antibody-drug conjugates produce clinically beneficial effects on Cath-D-expressing cells when administered to a patient, such as, for example, a patient with a Cath-D-expressing cancer, typically when administered alone but also in combination with other therapeutic agents.

In typical embodiments, an anti-Cath-D antibody is conjugated to a cytotoxic agent, such that the resulting antibody-drug conjugate exerts a cytotoxic or cytostatic effect on a Cath-D-expressing cell (e.g., a Cath-D-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-Cath-D antibody can be conjugated to a cytotoxic agent such as a chemotherapeutic agent or a toxin (e.g., a cytostatic or cytocidal agent such as, for example, abrin, ricin A, *pseudomonas* exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and -carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etoposide phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone. In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-Cath-D antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-Cath-D antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amrnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

Diagnostic Uses:

A further aspect of the invention relates to an anti-Cath-D antibody of the invention for diagnosing and/or monitoring a cancer disease and other diseases in which CathD levels are modified (increased or decreased).

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as $I^{123}$, $I^{124}$, $In1^{11}$, $Re^{186}$, $Re^{188}$. Antibodies of the invention may be also labelled with a spin label for nuclear magnetic resonance (NMR) imaging (also known as magnetic resonance imaging, MRI), such as iodine-123, iodine-131, indium-ill, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for diagnosing and staging of cancer diseases associated with Cath-D overexpression. Cancer diseases associated with Cath-D overexpression typically include but are not limited breast cancer, melanoma, ovarian cancer, lung cancer, liver cancer, pancreatic cancer, endometrial cancer, head and neck cancer, bladder cancer, malignant glioma.

Antibodies of the invention may be useful for diagnosing diseases other than cancers for which Cath-D expression is increased such as Alzheimer's disease.

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with Cath-D overexpression, and in a preferred embodiment from breast cancer, melanoma, ovarian cancer, lung cancer, liver cancer, pancreatic cancer, endometrial cancer, head and neck cancer, bladder cancer, malignant glioma. Therefore, biological samples encompass clinical samples, cells in culture, cell supernatants, cell lysates, serum, plasma, biological fluid, and tissue samples.

Therapeutic Uses:

Antibodies, fragments or immunoconjugates of the invention may be useful for treating any disease associated with Cath-D overexpression preferentially cancers. The antibodies of the invention may be used alone or in combination with any suitable agent.

An anti-Cath-D antibody of the invention may be used as treatment of hyperproliferative diseases associated with Cath-D overexpression.

Examples of such diseases associated with Cath-D overexpression encompasses breast cancer, melanoma, ovarian cancer, lung cancer, liver cancer, pancreatic cancer, endometrial cancer, head and neck cancer, bladder cancer, malignant glioma.

In a particular embodiment, breast cancer is an estrogen-receptor positive (ER+) hormono-resistant breast cancer or a triple-negative (ER– and PR–, HER2-non amplified) breast cancer.

In each of the embodiments of the treatment methods described herein, the anti-Cath-D antibody or anti-Cath-D antibody-drug conjugate is delivered in a manner consistent with conventional methodologies associated with management of the disease or disorder for which treatment is sought. In accordance with the disclosure herein, an effective amount of the antibody or antibody-drug conjugate is administered to a patient in need of such treatment for a time and under conditions sufficient to prevent or treat the disease or disorder.

Thus, an aspect of the invention relates to a method for treating a disease associated with the overexpression of Cath-D comprising administering a patient in need thereof with a therapeutically effective amount of an antibody, fragment or immunoconjugate of the invention. In this context, the term "treating" or "treatment", as used herein, means reversing, alleviating, inhibiting the progress of, or preventing the disorder or condition to which such term applies, or one or more symptoms of such disorder or condition. According to the invention, the term "patient" or "patient in need thereof" is intended for a human affected or likely to be affected with disease associated with the overexpression of Cath-D.

By a "therapeutically effective amount" of the antibody of the invention is meant a sufficient amount of the antibody to treat said disease associated with the overexpression of Cath-D such as a cancer (e.g. breast cancer), at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

In certain embodiments, an anti-Cath-D antibody or antibody-drug conjugate is used in combination with a second agent for treatment of a disease or disorder. When used for treating cancer, an anti-Cath-D antibody or antibody-drug conjugate of the invention may be used in combination with conventional cancer therapies such as, e.g., surgery, radiotherapy, chemotherapy, or combinations thereof.

Another aspect of the invention relates to an isolated human anti-Cath-D monoclonal antibody or a fragment thereof for use in a method for treating breast cancer.

The invention also relates to a method for treating breast cancer comprising administering a patient in need thereof with a therapeutically effective amount of an isolated human anti-Cath-D monoclonal antibody or a fragment thereof.

Pharmaceutical Compositions:

For administration, the anti-Cath-D antibody or antibody-drug conjugate is formulated as a pharmaceutical composition. A pharmaceutical composition comprising an anti-Cath-D antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits:

Finally, the invention also provides kits comprising at least one antibody of the invention. Kits containing antibodies of the invention find use in detecting Cath-D expression (increase or decrease), or in therapeutic or diagnostic assays. For instance, the IgG1 E2 and F1 antibodies recognize cellular cathepsin D by immunofluorescence. Kits of the invention can contain an antibody coupled to a solid support, e.g., a tissue culture plate or beads (e.g., sepharose beads). Kits can be provided which contain antibodies for detection and quantification of Cath-D in vitro, e.g. in an ELISA. Such antibody useful for detection may be provided with a label such as a fluorescent or radiolabel.

The invention will be further illustrated by the following figures and examples.

However, these examples and figures should not be interpreted in any way as limiting the scope of the present invention.

FIGURES

Figure 1C:
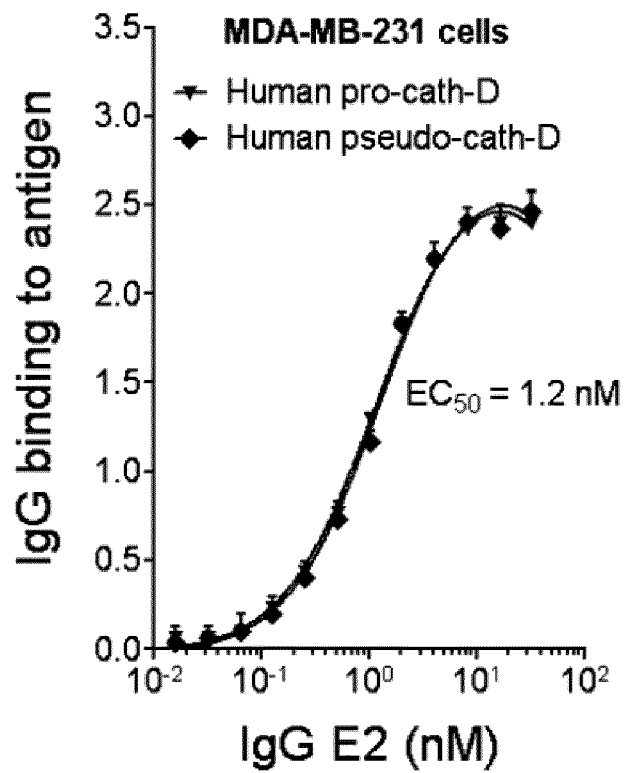

FIG. 1: Generation and characterization of anti-Cath-D scFv.

(A) Selection of monoclonal anti-Cath-D scFv by ELISA. ELISA performed on bacterial culture supernatants of the best scFv clones (8 on 400 screened clones) against human pro-, pseudo- and mature Cath-D is presented. The binding of scFv to Cath-D was detected with HRP-labeled anti-Myc antibody. BSA, negative antigen; IR (irrelevant): negative scFv from the screen. ScFv (F6, H7, F1, E12, E2) were isolated with mature Cath-D antigen, and scFv (D7, B1 and H2) with pseudo-Cath-D antigen.

(B) Binding of anti-Cath-D scFv to human Cath-D from MDA-MB-231 BCC. The binding of anti-Cath-D scFv was assayed by ELISA on secreted human pro-cath-D, auto-activated pseudo-cath-D, and cellular human Cath-D from MDA-MB-231 BCC using anti-His conjugated to HRP. BSA, negative antigen; IR, negative scFv.

(C) Binding of IgG1 F1 and E2 to pro-Cath-D and pseudo-Cath-D from MDA-MB-231 BCC. Sandwich ELISA was performed at pH 7 on conditioned medium of MDA-MB-231 BCC (CM; 7 days in the presence of FCS; acidified or not) added to pre-coated anti-pro-Cath-D M2E8 mouse monoclonal antibody in the presence of increasing concentrations of IgG1 F1 (top Panel) or IgG1 E2 (bottom Panel). The binding of IgG1 F1 and IgG1 E2 to pro-Cath-D was revealed with an anti-human Fc antibody conjugated to HRP. $EC_{50}$ values are shown.

Figure 2:
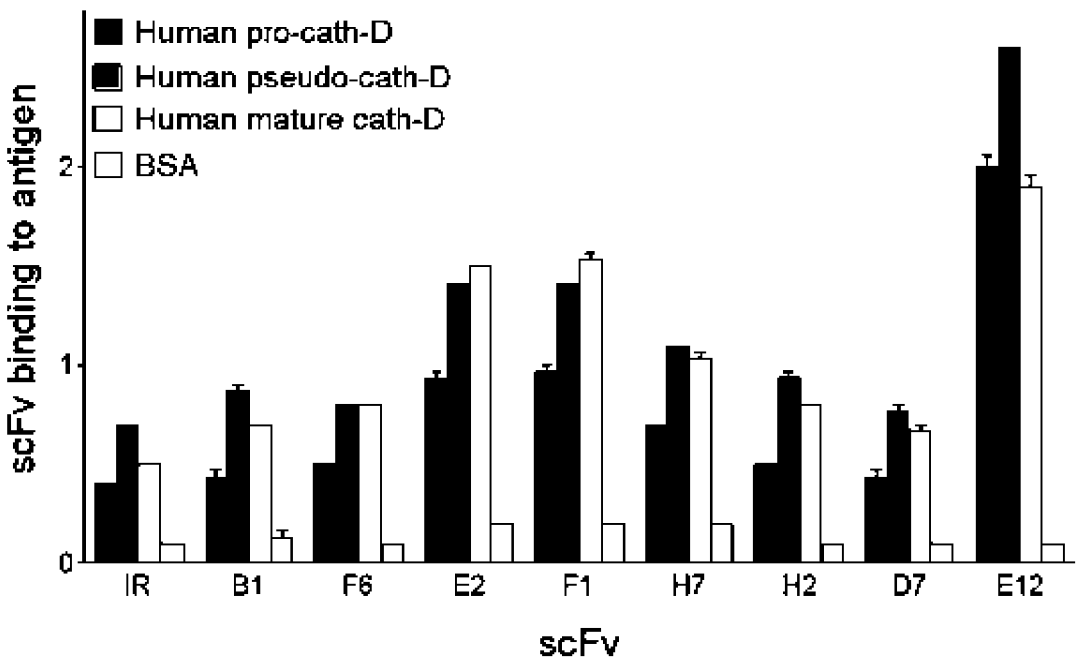
Figure 2:
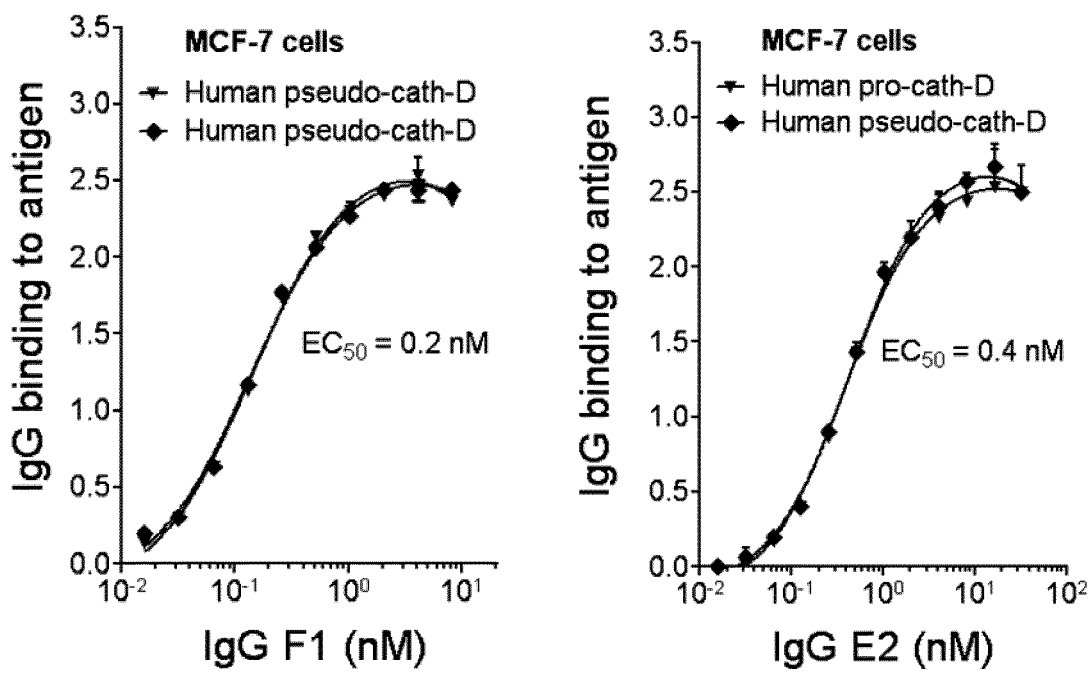

FIG. 2: Characterization of human anti-Cath-D IgG1 F1 and E2 in $ER^+$ BCC.

(A) Binding of anti-Cath-D scFv to human Cath-D from MCF-7 BCC. The binding of anti-Cath-D scFv was assayed by ELISA on secreted human pro-cath-D, auto-activated pseudo-cath-D, and cellular human Cath-D from MCF-7 BCC using anti-His conjugated to HRP. BSA, negative antigen; IR, negative scFv.

(B) Binding of IgG1 F1 and E2 to pro-Cath-D and pseudo-Cath-D from MCF-7 BCC. Sandwich ELISA was performed at pH 7 on conditioned medium (CM; 7 days in the presence of FCS; acidified or not) of MCF-7 BCC added to pre-coated anti-pro-Cath-D M2E8 mouse monoclonal antibody in the presence of increasing concentrations of IgG1 F1 (left Panel) or IgG1 E2 (right Panel). The binding of IgG1 F1 and IgG1 E2 to pro-Cath-D was revealed with an anti-human Fc antibody conjugated to HRP. $EC_{50}$ values are presented.

FIG. 3: Inhibitory effects of anti-Cath-D scFv on pseudo-Cath-D proteolytic activity. A summary of Ki±SD (n=3) is presented.

FIG. 4: Inhibitory effects of the scFv on mature Cath-D proteolytic activity. A summary of Ki±SD (n=3) is presented.

Figure 5:
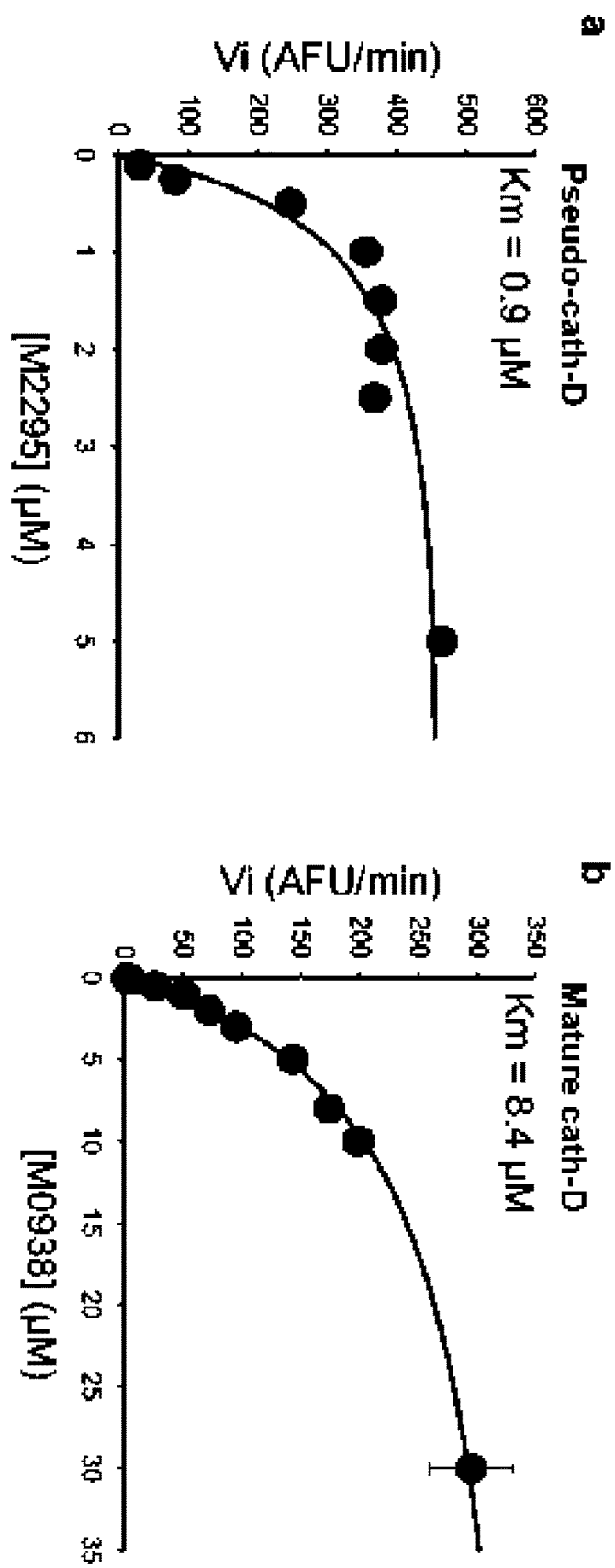

FIG. 5: Michaelis-Menten kinetics of pseudo-Cath-D and mature Cath-D with M0938 and M2295 substrates. Best-fit values of pseudo-Cath-D (A) and mature Cath-D (B) according to the Michaelis-Menten equation are Vmax=531±28 AFU/min; Km=0.9±0.1 µM and Vmax=374±22 AFU/min; Km=8.4±1.2 µM, respectively.

Figure 6:
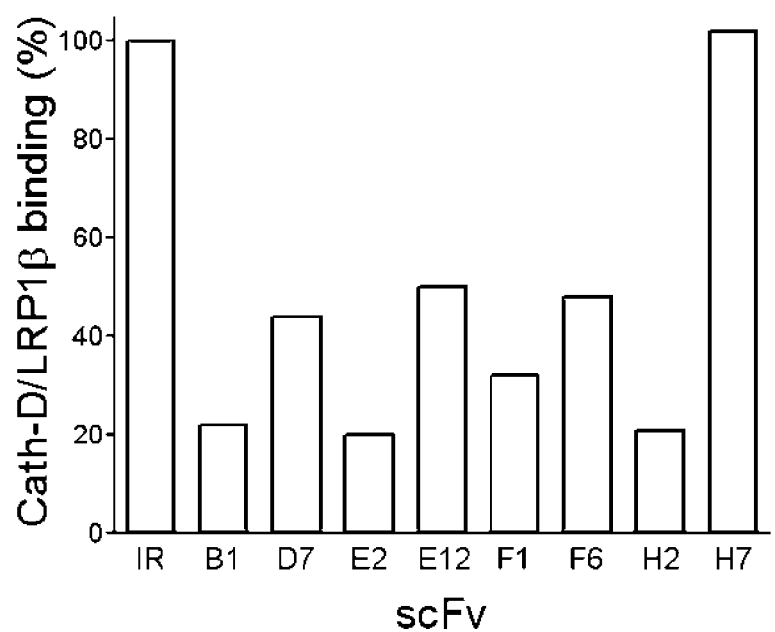

FIG. 6: Effect of anti-Cath-D scFv on the binding of pro-Cath-D to GST-LRP1β fragment. Radio-labeled pro-Cath-D pre-incubated with anti-Cath-D or irrelevant scFv was loaded on beads containing GST-LRP1 β (307-479) (amino acids 307-479 of LRP1β extracellular domain). The quantification of the ratio of pro-Cath-D bound to GST-LRP1β in presence of scFv relative to total GST-LRP1β is represented as percentage (%) relative to irrelevant scFv (IR, negative scFv from the screen).

FIG. 7: Interaction of human Cath-D with scFv F1 and E2, and IgG1 F1 and E2

(A) Competitive ELISA between IgG1 and scFv F1 and E2. Sandwich ELISA was performed with conditioned medium (CM; 7 days in the presence of FCS) from MDA-MB-231 BCC added to pre-coated anti-pro-Cath-D M2E8 antibody in the presence of IgG1 F1 or E2 (around $EC_{50}$ value; 40 ng/ml; 0.27 nM), and increasing concentrations (0.04-10 µg/ml) of scFv F1, E2 or IR (negative scFv from the screen). The binding of IgG1 F1 or IgG1 E2 to pro-Cath-D was revealed with an anti-human Fc antibody conjugated with HRP.

(B) Epitope of scFv F1 and E2 on mature Cath-D. Schematic representation of the human Cath-D 52 kDa pro-Cath-D. The locations of the 4-kDa Cath-D pro-fragment, 14-kDa light, and of the 34-kDa heavy mature chains are indicated. The intermediate 48-kDa form corresponds to non-cleaved 14+34 kDa chains. According to [72], 1 corresponds to the first amino acid in mature Cath-D. The positions of the 2 aspartic acids of the catalytic site are shown, as are the 2 glycosylated chains carrying M6P motifs. K, kilodalton.

Figure 8A:
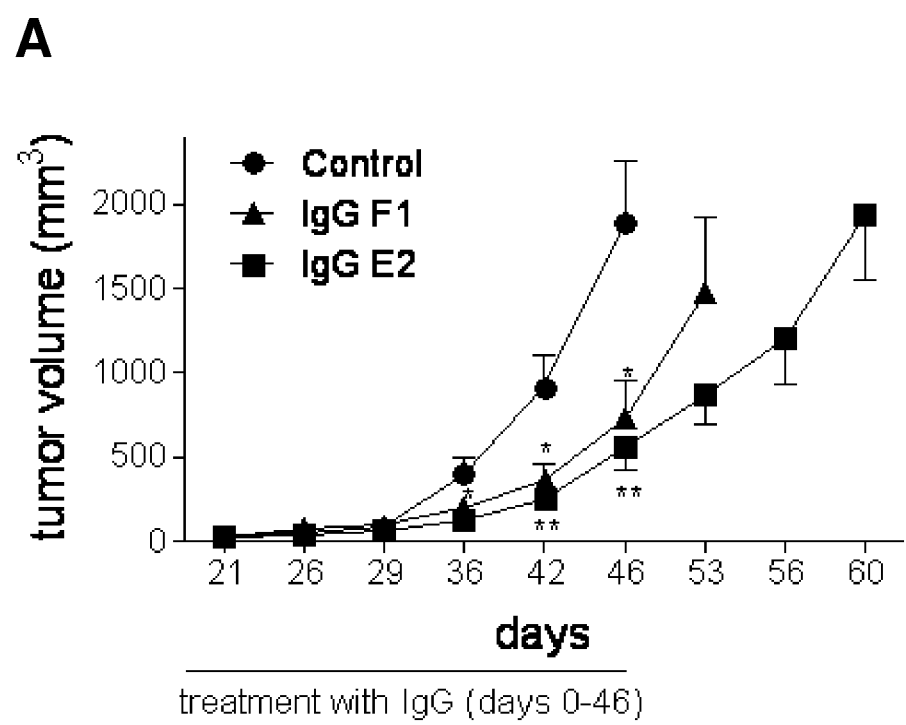

FIG. 8: Effect of anti-Cath-D IgG1 F1 and E2 on MDA-MB-231 tumor growth and survival in athymic mice.

(A) Growth of MDA-MB-231 xenografts in mice treated with anti-Cath-D IgG1 F1 and E2. MDA-MB-231 cells (1.5 $10^6$ cells) were mixed (ratio 1:1) with Matrigel and subcutaneously injected into flank of athymic mice. One day later, mice were injected intra-peritoneally with IgG1 F1 and E2 (15 mg/kg) or NaCl three times per week for 45 days. Mice were sacrificed when tumor volume reached 2000 mm3, and tumor growth curve was stopped. Tumor growth was monitored twice a week. Tumor volume is shown in $mm^3 \pm SEM$ (n=8 for control and IgG F1; n=7 for IgG E2). **, $p<0.01$; *, $p<0.05$; Student's t-test.

(B) Kaplan-Meier curve. Statistical differences were assessed using the log rank test ($p<0.05$ for IgG F1 and IgG E2).

Figure 9:
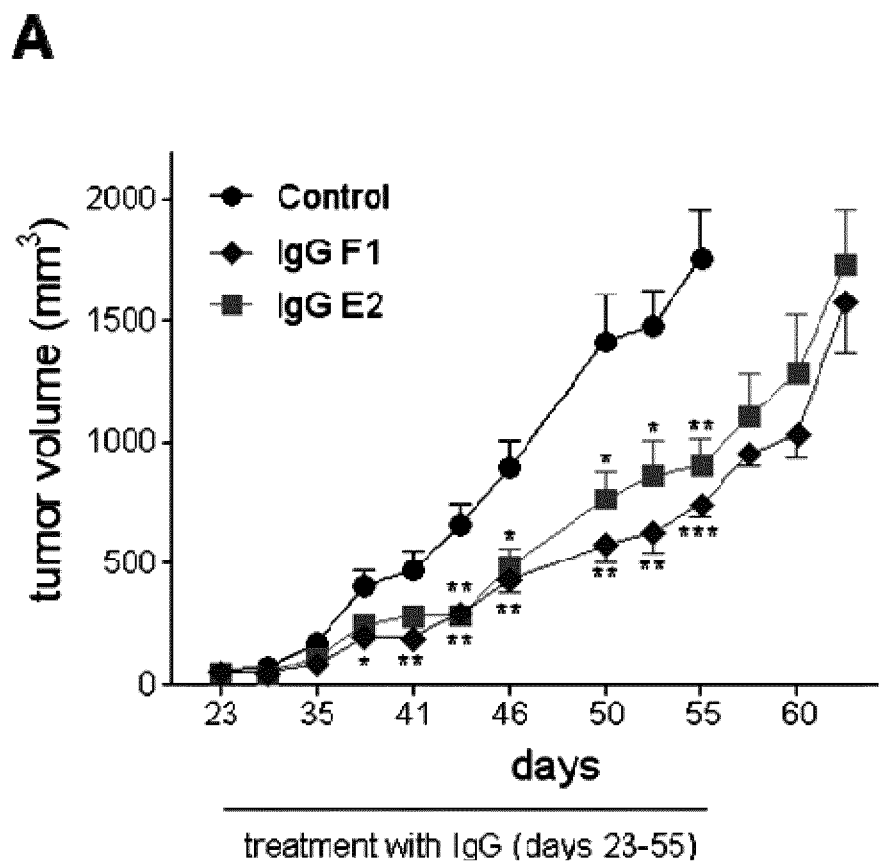

FIG. 9: Effect of anti-cath-D IgG F1 and E2 on MDA-MB-231 established tumor growth and survival in athymic mice (A) Growth of MDA-MB-231 xenografts in mice treated with anti-Cath-D IgG1 F1 and E2. MDA-MB-231 cells (1.5 $10^6$ cells) were mixed (ratio 1:1) with Matrigel and subcutaneously injected into flank of athymic mice. When tumor volume reached 50 $mm^3$, mice were injected intra-peritoneally with IgG1 F1 (15 mg/kg), IgG E2 (15 mg/kg), or NaCl three times per week for 32 days. Mice were sacrificed when tumor volume reached 2000 $mm^3$, and tumor growth curve was stopped. Tumor growth was monitored twice a week. Tumor volume is shown in $mm^3 \pm SEM$ (n=8 for control; n=6 for IgG F1 and IgG E2). *, $p<0.001$; , $p<0.01$; *, $p<0.05$; Student's t-test.

(B) Kaplan-Meier curve. Statistical differences were assessed using the log rank test ($p<0.0005$ for IgG F1 and IgG E2).

Figure 10:
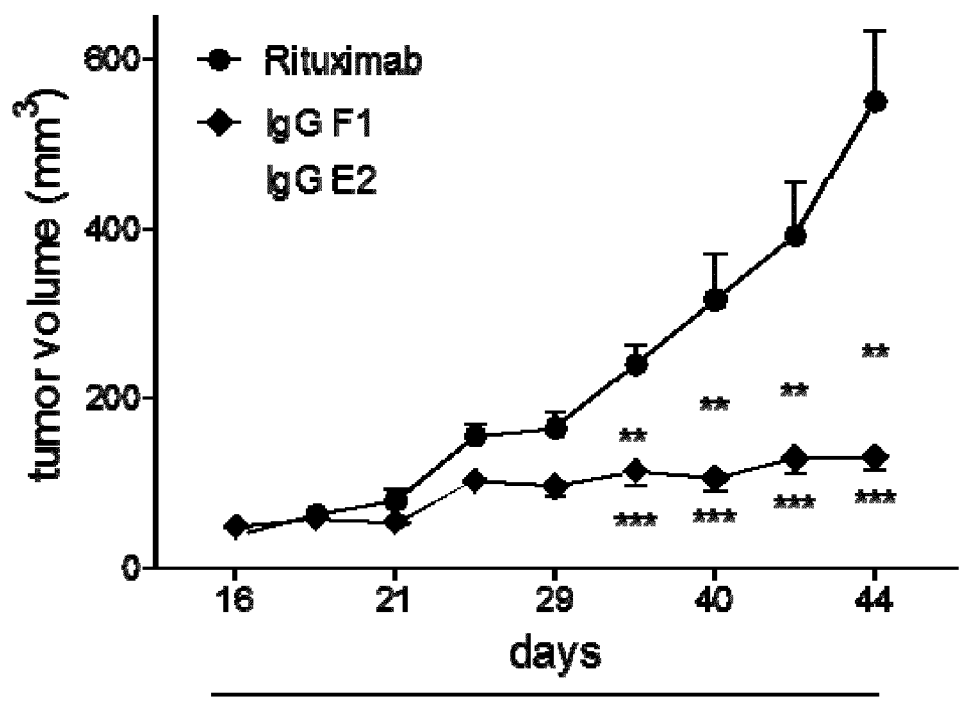

FIG. 10: Effect of anti-Cath-D IgG1 F1 and E2 on MDA-MB-231 tumor size and macroscopic appearance.

Tumor growth of MDA-MB-231 xenografts in mice treated with anti-Cath-D IgG1 F1 and E2, or control rituximab. MDA-MB-231 cells (1.5 $10^6$ cells) were mixed (ratio 1:1) with Matrigel and subcutaneously injected into flank of athymic mice. When tumor volume reached 50 $mm^3$, mice were injected intra-peritoneally with IgG1 F1 (15 mg/kg), IgG E2 (15 mg/kg), or rituximab (IgG control, 15 mg/kg) three times per week for 28 days. Mice were sacrificed at day 44 when control tumor volume reached 600 $mm^3$. Tumor growth was monitored twice a week. Tumor volume is shown in $mm^3 \pm SEM$ (n=9 for rituximab, IgG F1 and IgG E2). *, $p<0.001$; , $p<0.01$; Student's t-test.

EXAMPLE: ANTIBODY TARGETING OF THE PROTEASE CATHEPSIN D IN THE TUMOR MICROENVIRONMENT INHIBITS BREAST CANCER GROWTH

Material & Methods
Materials:

LRP1β(307-479) was generated by inserting PCR-amplified cDNA encoding LRP1β(307-479) from pYESTrp2-LRP1β(307-479) identified by a two-yeast hybrid assay into pGEX-4T-1 previously digested by EcoRI [29]. The pGEX-4T-1-Cath-D constructs were obtained by inserting PCR-amplified cDNA encoding human 52-, 48-, 34-, 14-, or 4-kDa Cath-D chains into pGEX-4T-1 previously digested with EcoRI [29]. The mouse anti-human Cath-D monoclonal antibody M2E8, used for sandwich ELISA interacts only with 52-kDa pro-Cath-D, and not with 48-kDa or 34-kDa Cath-D [46]. The anti-human Cath-D monoclonal antibody (BD Biosciences) recognizing 52-, 48- and 34-kDa forms of Cath-D, the anti-human Cath-D antibody (ABCAM; ab75811) recognizing the 14-kDa Cath-D light chain, and the anti-human Cath-D antibody recognizing the 4-kDa Cath-D pro-domain kindly provided by Pr. M. Fusek (Oklahoma Medical Research Foundation, Oklahoma City, Okla., U.S.A.) [18] were used for immunoblotting. The goat polyclonal anti-human Fc antibody conjugated to HRP (A0170), mouse monoclonal HRP anti-his (A7058), cellular Cath-D (from human liver), D-erythro-ceramide C8 1-phosphate (C8355), pepstatin A, BSA, and crystal violet were purchased from (Sigma Aldrich). The polyclonal anti-mouse cathD (sc-6486) and the monoclonal anti-c-Myc antibody conjugated with HRP (9E10) were purchased from (Santa Cruz Biotechnology), the Rituximab (anti-CD20 antibody) from Roche, and the monoclonal anti-M13 antibody conjugated with HRP (27942101) from (GE Heathcare). The fluorogenic peptide substrate for pseudo-Cath-D (M2295: Ac-Glu-Asp(EDANS)-Lys-Pro-Ile-Leu-Phe-Phe-Arg-Leu-Gly-Lys(DABCYL)-Glu-$NH_2$) was purchased from (Sigma Aldrich), and the fluorogenic peptide substrate for mature Cath-D (M0938: MCA-Gly-Lys-Pro-Ile-Leu-Phe-Phe-Arg-Leu-Lys-DNP-Arg-$NH_2$) from (BACHEM). Recombinant human 52-kDa pro-Cath-D was purchased from (R&D Systems). Matrigel was purchased from (BD Biosciences).

Cell Lines and Conditioned Media and Cell Lysates:

MDA-MB-231, MCF-7 and T47D BCC and wild-type MEF (mouse embryonic fibroblast) were cultured in DMEM with 10% fetal calf serum (FCS, GibcoBRL, Life technologies, Carlsbad, Calif., USA). To produce conditioned medium and cell lysate, cells were grown to 90% confluence in DMEM medium 10% FCS. Conditioned medium (24 h in absence of FCS or 7 days in presence of FCS) was removed and centrifuged at 800×g for 10 min. Cells were lysed by 5 thawing-freezing cycles in 1 ml PBS, and cell lysate was isolated after centrifugation at 13,000×g for 20 min at 4° C.

Stable Transfection of shRNA in MDA-MB-231 BCC:

MDA-MB-231 BCC were transfected with anti-Cath-D shRNA1 or shRNA2 expression vectors (Invivogen) using Nucleofector Technology (Amaxa biosystems) according to the manufacturer's instructions and clones resistant to Blasticidin (10 µg/ml) were isolated. Clone S1C4 transfected with anti-Cath-D shRNA1 and clone S2C6 transfected with anti-Cath-D shRNA2 were the best clones selected for Cath-D silencing.

Auto-Activation of 52-kDa Pro-Cath-D to 51-kDa Pseudo-Cath-D:

To produce the 51-kDa pseudo-Cath-D, recombinant 52-kDa pro-Cath-D (10 μg) was auto-activated for 15 min at 37° C. in 30 μl MES buffer 25 mM, [pH 6.5] plus 2 μl of 1 M Na-acetate buffer [pH 3.5]/2 M NaCl to a 3.9 final pH and then neutralized to pH 7 with 50 μl de $NaH_2PO_4$ 2N. In other experiments, the 51-kDa pseudo-Cath-D was directly produced from 52-kDa secreted into the conditioned medium of BCC as previously described [71]. To auto-activate in vitro the secreted pro-Cath-D, culture medium conditioned in DMEM with 10% FCS was incubated at 37° C. for 1 hour at pH adjusted to 3.5 by the addition of 1N HCl and then neutralized to pH 7.4 with 1N NaOH.

Antibody Phage Display:

The HuscI library uses a single framework optimized for high level expression [37]. The diversity was restricted to five amino acids (Y,N,D,G,S) and introduced in the six CDRs at the positions corresponding to the most contributing residues of the paratope [38]. The antigens used were commercial human 51-kDa pseudo-cath D and human cellular mature (34+4-kDa) Cath-D. The negative antigen was BSA. The selection of scFv from HUSCI library was performed as described previously [37]. Pseudo-Cath-D, mature Cath-D, or BSA was coated at 100 ng/well in PBS (pH 7.4) on 96-well plates (Nunc Maxisorp) overnight at 4° C. After washing (PBS/tween 0.1%), non-specific binding sites were blocked with 1% gelatin/PBST, and $10^{10}$ scFv phages/ml were applied to each well for 2 h at room temperature as described previously [37]. Revelation was done using anti-M13 antibody conjugated to HRP. To enrich the polyclonal scFv population in Cath-D-binders, this experiment was repeated in four successive selection rounds. Polyclonal scFv enriched in Cath-D-binders were transformed into BL21 (DE3)/pLysS bacteria. BL21 (DE3)/pLysS colonies (total 400) were picked into the 96-well microtiter plates to produce scFv by auto-induction and lysed as described previously [37]. Human pseudo-Cath-D, mature Cath-D or BSA was coated at 100 ng/well on 96-well plate overnight at 4° C. After washing (PBS/tween 0.1%), and blocking (1% gelatin/PBST), whole bacterial lysate containing monoclonal scFv was applied for 2 h at 4° C. Revelation was done using anti-c-Myc antibody conjugated to HRP.

Sequencing of ScFv Antibody Genes:

Double strand phagemid DNAs were extracted from bacterial culture and expanded from each positive wells of monoclonal phage ELISA plates, and sequenced with T7 and T7-term primers (Eurofins Genomics).

Purification of scFv Antibody Fragments:

Shuffled scFv genes were subcloned into the expression vector PET23NN, which results in the addition of a hexahistidine tag at the C-terminal end of the scFv. The recombinant plasmid pET2NN-scFv was obtained and transformed in E. coli BL21 (DE3)/pLysS (Invitrogen) and was purified on a TALON-cobalt column according to the manufacturer's protocol. The recognition of purified scFv for Cath-D was performed by ELISA as described previously and revealed with anti-His conjugated to HRP.

Cloning and Expression of IgG:

ScFv (F1, E2 and E12) were sub-cloned in human IgG1, λ format and were expressed in (CHO) Chinese hamster ovary cell line and purified on protein-A HiTrap column (GE Healthcare) by Evitria AG.

GST-Pull-Down Assays:

[$^{35}$S]methionine-labeled pre-pro-Cath-D was obtained by transcription and translation using the TNT T7-coupled reticulocyte lysate system (Promega). GST-LRP1β(307-479) fragments were produced in *Escherichia coli* B strain BL21 using isopropyl-1-thio-β-D-galactopyranoside (1 mM) for 3 h at 37° C. GST fusion proteins were purified on glutathione-Sepharose beads (Amersham Biosciences). For pull-down assays, 20 μl of glutathione-Sepharose beads with immobilized GST fusion proteins were incubated overnight at 4° C. with [$^{35}$S]methionine-labeled proteins pre-pro-Cath-D pre-incubated with the scFv antibody in 500 μl PDB buffer (20 mM HEPES-KOH [pH 7.9], 10% glycerol, 100 mM KCl, 5 mM MgCl2, 0.2 mM EDTA, 1 mM DTT, 0.2 mM phenylmethylsulfonyl fluoride) containing 15 mg/ml BSA and 0.1% Tween 20. The beads were washed with 500 μl PDB buffer, and bound proteins were resolved by 15% SDS-PAGE, stained with Coomassie blue, and exposed to autoradiographic film.

Catalytic Activity Assay for Cath-D Activity and Steady-State Kinetics:

Cleavage reaction in 100 μl were carried out in 0.1 M 2-(N-morpholino)ethanesulfonic acid (MES) buffer [pH 6] containing D-erythro-ceramide C8 1-phosphate (10 μM), Cath-D (5 nM) and M2295 (fluorogenic peptide substrate for pseudo-Cath-D) or M0938 (fluorogenic peptide substrate for mature Cath-D). Kinetic parameters of pseudo-Cath-D and mature Cath-D (Km) were determined with M2295 or M0938 substrate tested at concentrations varying from (0.05 μM to 5 μM) and (0.05 μM to 30 μM), respectively. Reactions were run in white 96 half-well plates (Corning), and cleavage of substrate was measured in BMG Labtech Fluostar Omega spectrofluorometer. Km was determined using the Michaelis-Menten equation. Rate data were fitted to the single substrate kinetics models provided by the Enzyme Kinetics Module of SigmaPlot 12 software (Systat Software Inc., San Jose, USA), using nonlinear least-squares regression analysis. Rate data corresponding to the hydrolysis kinetics of two peptides were best fitted to the Michaelis Menten equation ($V_i=V_{max}*S/Km+[S]$). Ki value was calculated by re-fitting the data to a competitive enzyme-inhibition equation ($Vi=(Vmax*[S])/(Km(1+[I]/Ki)+[S])$). To allow visualization of fitting quality, the experimental data points are presented as plots along with the theoretical lines fitted by Enzyme Kinetics software. To assess the inhibitory effect of scFv on pseudo-Cath-D proteolytic activity, Cath-D (5 nM) was incubated at 37° C. (in a final volume of 100 μl) in 0.1 M MES buffer [pH 6] with D-erythro-ceramide C8 1-phosphate (10 μM) and M2295 substrate at 3 concentrations around the Km value. For each substrate concentration, various concentrations of scFv were used to determine the mechanism and the constant inhibition (Ki) for pseudo-Cath-D. Similar experiments were conducted with mature Cath-D with M0938 substrate.

Surface Plasmon Resonance (BIAcore):

The binding of human IgG1 F1 and E2 to various Cath-D isoforms (pseudo-Cath-D, mature Cath-D and pro-Cath-D) were measured at 25° C. by Surface Plasmon Resonance analysis using a T200 instrument (GE Healthcare, Uppsala, Sweden). Experiments were performed in HBS-EP buffer: 10 mM HEPES pH 7.4, 3 mM EDTA, 150 mM NaCl, and 0.005% non-ionic surfactant P20 (GE Healthcare) at 30 l/min. IgG1 was captured on the CM5 sensor chip surface using an anti-human Fc (GE Healthcare) according to the manufacturer's instructions. Cath-D diluted in HBS-EP buffer was injected at different concentrations from 0.6 nM to 160 nM over IgG1 and control flow cells. The association and the dissociation phases were followed by a regeneration step with 2M $MgCl_2$. Sensorgrams were corrected by subtracting the control flow cell signal. Data were globally fitted to a conformation change model using the BIAevaluation version 4.1.1 software. For reverse scheme analysis, pseudo-Cath-D was covalently immobilized by amine coupling on CM5 sensor chip surface at 680 RU. A range of concentrations (0.5 nM-128 nM) of IgG1 F1 or E2 was injected on pseudo-Cath-D. Sensor grams were globally fitted by a bivalent model.

ELISA and Immunoprecipitation:

For sandwich ELISA, mouse monoclonal anti-human pro-Cath-D M2E8 antibody in PBS (500 ng/well) [46] was coated in 96-well plates overnight at 4° C. After blocking the non-specific sites with PBS 1x/tween 0.1%/BSA 1%, cell lysate or conditioned medium was applied for 2 h at 4° C. After washing in PBS/tween 0.1%, serial dilutions of anti-cathD IgG1 E2 or F1 was added for 2 h at 4° C. Revelation was done using goat anti-human Fc antibody conjugated to HRP. Immunoprecipitation was carried out on cell extract (1 mg) incubated overnight at 4° C. with 3 µg anti-Cath-D (IgG1 E2 or F1) monoclonal antibody, and then with 50 µl 10% protein G-Sepharose for 2 h at 4° C. on a shaker. The Sepharose beads were washed 3 times in PBS, boiled for 5 min in SDS sample buffer, and analysed by SDS-PAGE. In other experiments, immunoprecipitation was performed using GST-Cath-D fusion proteins produced in *Escherichia coli* B strain BL21 using isopropyl-1-thio-b-D-galactopyranoside (1 mM) for 3 h at 37° C. The resulting proteins were submitted to 12% SDS-PAGE followed by anti-Cath-D immunoblotting.

Outgrowth, Clonogenic and Wound Healing Assays:

For outgrowth assays, 50,000 MDA-MB-231 BCC embedded at 4° C. in 200 µl Matrigel (8 mg/ml) in presence of anti-Cath-D IgG1 E2 or F1 or with irrelevant anti-CD20 IgG1 (100 µg/ml final) were added to a pre-set layer of Matrigel (200 µl containing these IgG1 at 100 µg/ml final) in 24-well plates and covered with 500 µl DMEM+10% FCS containing IgG1 at 100 µg/ml final for 7 days [14]. For clonogenic assays, 300 MDA-MB-231 BCC were plated in 6-well plates in DMEM+10% FCS and treated with anti-Cath-D IgG1 F1 or E2, or with irrelevant anti-CD20 IgG1 every 48 h. In wound healing assay, 100,000 cells were seeded in 24-well plates and grown at 37° C. in DMEM with 10% FCS. After 24 h, a wound was generated by scratching each monolayer with a pipette tip. Cells were then incubated in DMEM with 10% FCS with anti-Cath-D IgG1 F1 or E2 or with irrelevant anti-CD20 IgG1 (100 µg/ml final). Wound closure was captured by a Nikon ECLIPSE TS 100 microscope and an Olympus SP-510 UZ camera.

In Vivo Tumor Growth:

In vivo experiments were performed in compliance with the French regulations and ethical guidelines for experimental animal studies in an accredited establishment (Agreement No. C34-172-27). Six-week-old female BALB/c nude mice (Harlan, Le Malourlet, France) were implanted with $1.5\times10^6$ MDA-MB-231 BCC s.c. on either flank. Cells were prepared by harvesting in the log phase of growth; they were washed in PBS and mixed 1:1 with Matrigel. Mice were randomly separated for treatment groups (n=10) on the day of implantation. Mice were treated IgG1 F1 (15 mg/kg), IgG1 E2 (15 mg/kg), rituximab (15 mg/kg) or NaCl (3 times per week) by intraperitoneal. Tumors were measured using a caliper and volume was calculated using the formula V=(tumor length tumor width tumor depth)/2.

Results

Selection and Functional Screenings of Anti-Cath-D scFv by Phage Display:

Human recombinant 51-kDa pseudo-Cath-D with an open catalytic site and human purified liver 34+14-kDa mature Cath-D were used as immunogen for the isolation of human antibodies from the phage antibody HuscI library [37]. This library uses a single framework optimized for high level expression [37]. The diversity was restricted to five amino acids (Y,N,D,G,S) introduced in the six CDRs at position corresponding to the most contributing residues of the paratope [38]. Polyclonal antibodies in scFv format showing specific binding by ELISA for immobilized pseudo-Cath-D or mature Cath-D were isolated and enriched from the library by 4 rounds of biopanning [37]. We selected 8 monoclonal scFv binding both to pro-Cath-D, pseudo-Cath-D and mature Cath-D by ELISA (FIG. 1A). These monoclonal scFv were purified. ELISA analysis revealed that purified scFv bound to human secreted pro-Cath-D, pseudo-Cath-D, and cellular Cath-D from triple-negative MDA-MB-231 BCC (FIG. 1B) and ER$^+$ MCF-7 BCC (FIG. 2A), and cross-reacted with murine Cath-D from MEF cells (80% identity between the two mature proteins). The 8 scFv were characterized in terms of their Ki values for the inhibition of the proteolytic activity of pseudo-Cath-D (FIG. 3; FIG. 5) and of mature Cath-D (FIG. 4; FIG. 5) at pH 6. The more potent scFv inhibiting pseudo-Cath-D and mature Cath-D proteolytic activity were F1, E2, E12 and H2 (Table 3). The 8 scFv were also screened for their ability to inhibit the interaction of pro-Cath-D to the LRP1 fibroblastic receptor in GST pull-down assay [29] (FIG. 6). All scFv except H7 inhibited the binding of pro-Cath-D to GST-LRP1β fragment by (50-79%) (FIG. 6; Table 3). Based on these two functional screenings, we followed our experiments with F1, E2 and E12 scFv that both inhibited the Cath-D proteolytic activity at pH 6 and its binding to LRP1 (Table 3).

TABLE 3

Inhibition of Cath-D proteolytic activity and/or Cath-D/LRP1 interaction by anti-Cath-D scFv. The constant inhibition (Ki) for pseudo-Cath-D and mature Cath-D proteolytic activity, and the inhibition of pro-Cath-D/LRP1β interaction (%) are presented for each anti-Cath-D scFv.

| | scFv | | | | | | | |
|---|---|---|---|---|---|---|---|---|
| | B1 | F6 | E2 | F1 | H2 | H7 | D7 | E12 |
| Ki ± SD (nM) of human pseudo-cath-D | N.D | 326 ± 80 | 754 ± 37 | 212 ± 86 | 675 ± 18 | N.D | N.D | 574 ± 90 |
| Ki ± SD (nM) of human mature cath-D | 19 ± 6.3 | N.D | 24 ± 7.4 | 100 ± 29 | 400 ± 89 | 100 ± 34 | N.D | 2.2 ± 0.8 |
| (%) Inhibition of LRP1/cath-D binding | 78 | 52 | 79 | 68 | 79 | 0 | 56 | 50 |

In Vitro Characterization of Anti-Cath-D IgG1:

Anti-Cath-D scFv (F1, E2, E12) were cloned as full human IgG1, λ, produced in CHO cells and purified from culture medium by affinity chromatography (EVITRIA). Purified IgG1 F1, E2, and E12 were analysed by Coomassie staining. The binding capacity of IgG1 F1 and IgG1 E2 to Cath-D secreted from MDA-MB-231 BCC was validated by sandwich ELISA with $EC_{50}$ of 0.3 nM and 0.4 nM, respectively. By contrast, scFv E12 lost its binding activity under the IgG1 format in ELISA. Similar binding of IgG1 F1 and E2 was obtained for Cath-D secreted by MCF-7 BCC (FIG. 2B). Since tumors exhibit acidic pH in their microenvironment [23-25], the binding of IgG F1 and E2 to Cath-D secreted from MDA-MB-231 BCC was analyzed at different pH. IgG F1 and E2 bound to immobilized Cath-D with comparable affinities over a pH range of 7.5 to 5.5. The binding capacity of IgG1 F1, E2, and E12 was analysed on cellular Cath-D from MDA-MB-231 and MCF-7 cell extracts by immunoprecipitation. Both IgG1 F1 and E2 immunoprecipitated cellular Cath-D from MDA-MB-231 and MCF-7 cells, while IgG E12 was inefficient. The binding affinity of IgG1 F1 and E2 to pseudo-Cath-D, mature Cath-D and pro-Cath-D was quantified by plasmon surface resonance. IgG1 F1 showed the best dissociation constant $K_D$ for all Cath-D isoforms compared to IgG1 E2. The $K_D$ for the pro-Cath-D was 10-fold lower for both IgG1 F1 and E2. Similar $K_D$ were obtained at pH 6, indicating that at the acidic pH of the tumor microenvironment, IgG1 F1 and E2 still bound to all Cath-D isoforms.

Figure 7A:
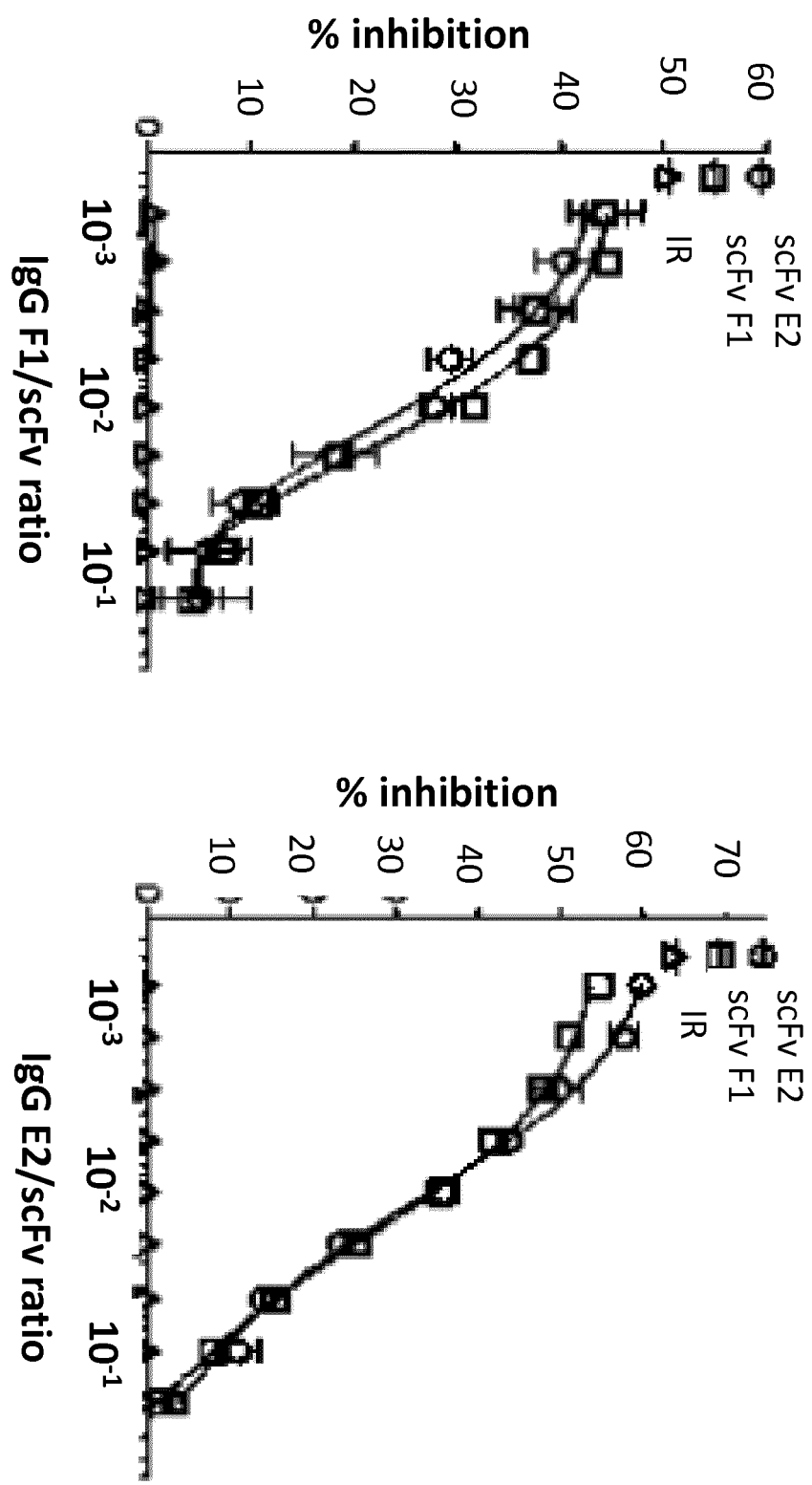
Figure 7B:
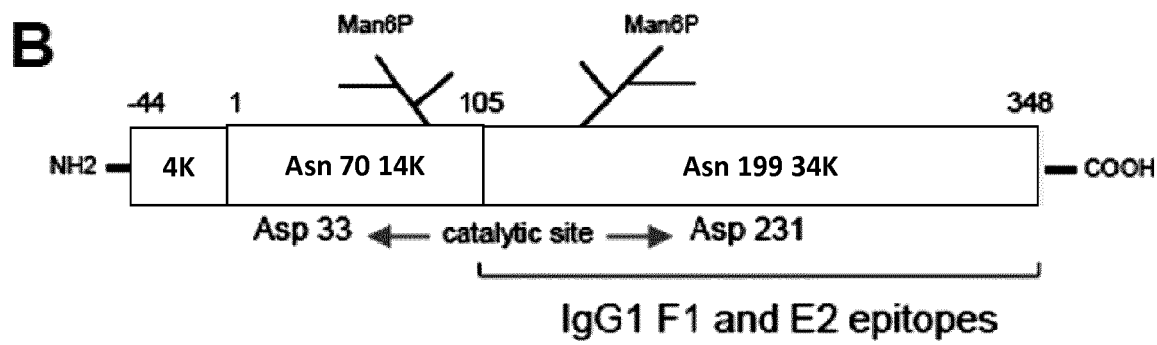

We next investigated the Cath-D epitope of IgG1 F1 and E2. Competitive ELISA indicated that IgG1 F1 and IgG1 E2 epitopes were overlapping (FIG. 7A). Using GST-Cath-D fusion fragments, IgG1 F1 and E2 immunoprecipitated both the 52-, 48- and 34-kDa Cath-D-GST, while the 4-kDa Cath-D-GST pro-fragment and the 14-kDa light chain Cath-D-GST were not recognized (FIG. 7B). Thus IgG1 F1 and E2 Cath-D epitopes are located on the heavy 34-kDa chain. Molecular docking model was performed on mature Cath-D three-dimensional structure [39]. According this model, anti-Cath-D scFv F1 and scFv E2 interact with the 34-kDa Cath-D chain at proximity of the catalytic aspartate 33 and 231 site, with a protruding L1 CDR inserting into the proteinase active site. The proposed epitopes ($^{128}$AAKFDG$^{134}$ (SEQ ID NO: 17); $^{172}$DPDAQPGG$^{179}$ (SEQ ID NO: 18)) located on the 34-kDa Cath-D are represented on the ribbon crystal structure of mature Cath-D at neutral [40], and acidic pH [41]. Dot blots experiments are ongoing to validate these epitopes.

Effect of Anti-Cath-D IgG1 F1 and E2 on BCC Behavior:

We first analysed the ability of the IgG1 F1 and E2 to affect in vitro BCC behaviors. IgG1 F1 and E2 significantly inhibited wound healing of MDA-MB-231 BCC, reduced the number and size of clones in clonogenic assay, and prevented the three-dimensional outgrowth of MDA-MB-231 BCC embedded in Matrigel. Silencing Cath-D by a shRNA approach (S1C4 and S2C6 clones), induced an inhibition of wound healing, clonogenic formation and outgrowth in Matrigel, supporting the key role of this protease in these processes. Importantly, IgG1 F1 and E2 were inefficient to affect wound healing when Cath-D was silenced in S1C4 and S2C6 clones. Finally, a significant inhibitory effect of IgG1 F1 and E2 was observed in wound healing assays performed with MCF-7 and T47D ER$^+$ BCC. Collectively our data strongly suggest that ability of IgG1 F1 and E2 to reduce BCC aggressiveness via the neutralization of extracellular Cath-D.

Figure 8B:
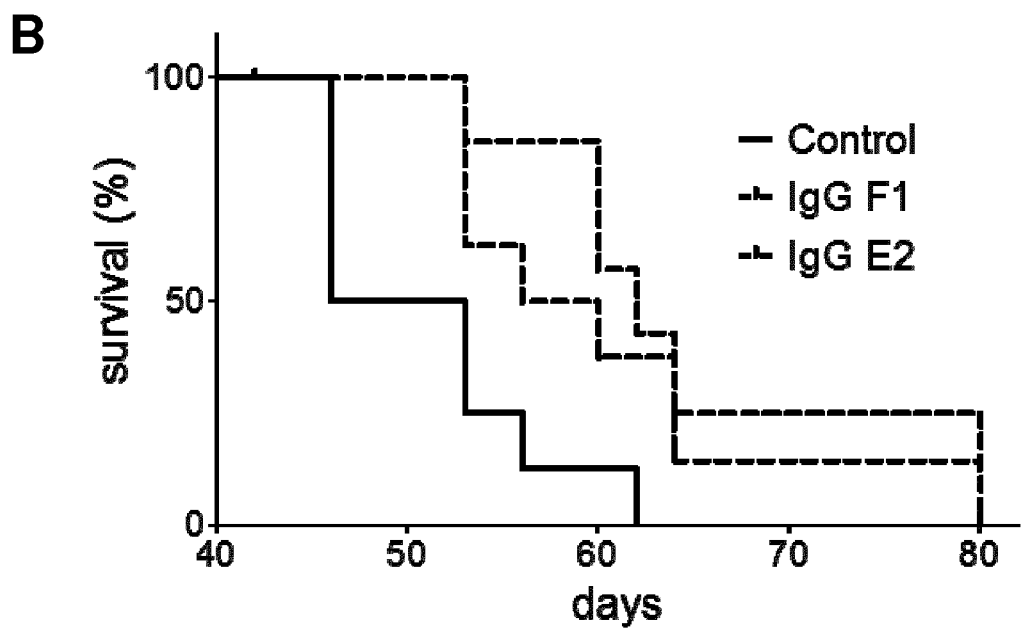

Effect of Anti-Cath-D Antibodies on Breast Tumor Progression:

In a setting experiment, 1 or 2 $10^6$ MDA-MB-231 BCC xenografts mixed with Matrigel (1:1) and established s.c. in Balb/c nude mice presented an exponential tumor growth reaching a tumor volume of 1000 mm$^3$ in 45 days with 100% uptake and adequate tumor size homogeneity (FIG. S8). Next, MDA-MB-231 xenografts (1.5 $10^6$ cells mixed (1:1) with Matrigel) in Balb/c nude mice were established s.c. and directly treated i.p. with IgG1 F1 and E2 (15 mg/kg, 3 times per week) for 45 days. Mice were sacrificed when tumor volume reached 2000 mm$^3$. Both IgG F1 and E2 treatment significantly inhibited tumor growth (FIG. 8A) and improved overall survival (FIG. 8B).

Figure 9B:
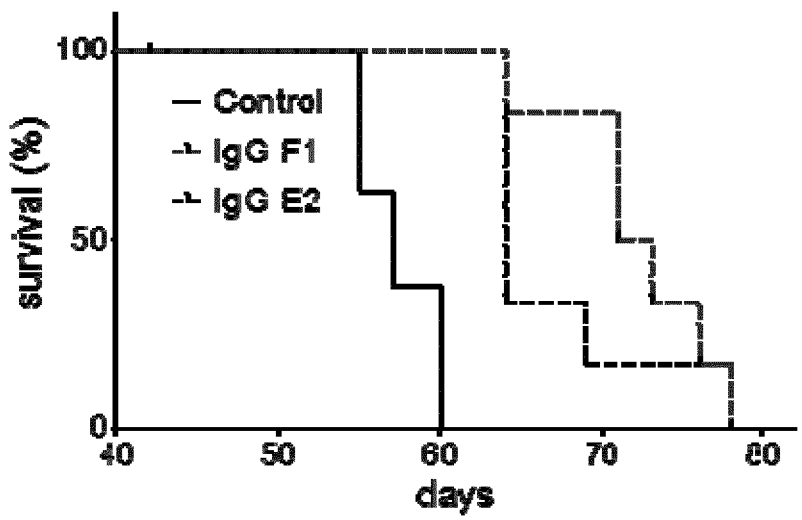

A similar inhibitory effect of IgG1 F1 and E2 was observed on MDA-MB-231 tumor growth (FIG. 9A) and improved overall survival (FIG. 9B) when IgG1 F1 and E2 (15 mg/kg, 3 times per week) were administrated i.p. for 32 days on 50 mm$^3$ established MDA-MB-231 tumor xenografts. In order to decipher the in vivo mechanism of action of IgG1 F1 and E2, the previous experiment performed on 50 mm$^3$ established MDA-MB-231 tumors was repeated and mice were sacrificed at day 44 after 28 days of treatment (FIG. 10).

Importantly, when using the anti-human CD20 rituximab antibody as a negative control that does not cross-react with mouse CD20, comparable tumor growth inhibitory effects were obtained compared to NaCl (FIG. 10A). Optical photography confirmed tumor size differences between rituximab group as compared to the anti-Cath-D IgG1 F1 and IgG E2 groups. Moreover, tumors from anti-Cath-D antibodies treated groups were less bloodstained compared to rituximab, suggesting a possible negative effect of IgG F1 and IgG E2 on tumor angiogenesis (data not shown).

Discussion

This report shows the ability to target and block Cath-D, expressed at elevated levels in the microenvironment of breast carcinomas, using anti-Cath-D human IgG1 F1 and E2. In vitro, these antibodies inhibited in vitro the wound healing, clonogenic formation and three-dimensional outgrowth of BCC, and in vivo decreased tumor growth of triple-negative BCC. It is worth noting that Cath-D is a ubiquitous key non-redundant member of the cathepsins essential for the catabolism of proteins in lysosomes and the maintenance of cellular homeostasis. Cath-D knock-out mice die shortly after birth with a neuronal ceroid lipofuscinosis (NCL) phenotype [42]. Congenital Cath-D mutations in humans leading to its reduced synthesis or the production of an enzymatically-inactive protein result in NCL [43]. Thus, human antibodies preferential targeting extracellular pathologic Cath-D (over intracellular Cath-D) are critical to circumvent off-target effects compared to specific cell-permeable small molecule inhibitors.

Our findings indicate that anti-Cath-D human IgG1 F1 and E2 recognize specifically the 34-kDa heavy chain of human Cath-D. It has been proposed that antibodies may preferentially target protruding loops at the rim of the substrate-binding cleft to interfere with the catalytic machinery of proteases without requiring long insertion loops [44]. The molecular docking of F1 and E2 scFv with mature cath-D three-dimensional structure strongly suggests that F1 and E2 scFv interact with the same protruding element proximal to the Cath-D aspartate catalytic site. Our competitive ELISA validated that IgG F1 and E2 epitopes are overlapped. This indicates a potential inhibition of substrate hydrolysis by an obstruction of substrate access to the active site or by an allosteric mechanism. Further studies are required to elucidate precisely the structural insight of the mechanisms of Cath-D inhibition by the two human anti-Cath-D antibodies.

So far no human antibody inhibiting both the Cath-D catalytic activity and its binding to the LRP1 fibroblastic receptor had yet been described. Hybridoma strategy previously led to the generation of high affinity monoclonal mouse anti-Cath-D antibodies. Garcia and colleagues immunized mice with 52-kDa pro-Cath-D purified from MCF-7 BCC cells to generate mouse monoclonal antibodies selective to human Cath-D [45]. Certain of these monoclonal mouse anti-Cath-D antibodies recognizing the 34-kDa heavy chain specifically inhibited the Cath-D proteolytic activity at pH 4.5, whereas those recognizing specifically the Cath-D pro-peptide did not [46]. Rochefort's group then developed a solid-phase two-site immunoenzymometric assay (IEMA) of the 52-kDa pro-Cath-D and its processed forms (48-kDa and 34-kDa proteins) in cytosols of breast cancer tissues, using two of these monoclonal antibodies (M1G8 and D7E3) directed against different epitopes of the 34-kDa chain [47, 48]. This two-site IEMA allowed the clinical evaluation of Cath-D as a poor prognostic marker in breast cancer associated with the metastatic risk and a shorter survival [8, 9]. So far, the potential anti-tumor effect of these anti-cath-D mouse antibodies remains uninvestigated. By contrast, Vetvicka's group developed mouse monoclonal peptide antibodies against amino acid stretch (aa 27-44) within the Cath-D pro-peptide that inhibited the growth of human breast tumors in athymic nude mice [49], but no further validation had never been yet published. Here, we used the antibody phage display technology, a convenient methodology for the isolation of human monoclonal antibodies needed for applications in humans [50]. Based on our previous work concerning Cath-D action in breast cancer [26, 29], the Cath-D-binders scFv were selected by two stringent functional screenings: their ability to inhibit Cath-D proteolytic activity and its binding to its LRP1 fibroblastic receptor. Importantly, the human scFv antibody format is suitable for incorporation of the binding specificity into therapeutic proteins [51, 52] and can easily be reformatted into intact IgG1, as we reported here. Intact immunoglobulins are a preferable format, due to their long circulatory half-life. Thus, the majority of therapeutic antibodies in oncology are human IgG1 isotypes (e.g. Herceptin and Cetumximab). IgG1 also allows engagement of immune effector cells through binding of Fc receptors (FcγR) expressed on NK cells, macrophages and leukocytes [53].

Cath-D is only one of a number of proteases that have been implicated in the remodeling of the tumor microenvironment. The matrix metalloproteinases have been extensively studied with many showing significant up-regulation in tumors [3]. Matrix metalloproteinase inhibitors that were developed showed promising preclinical results but ultimately yielded disappointing results in clinical trials. This was due, at least in part, to intricacies of their physiologic and patho-physiologic roles [54, 55]. Consequently, attention has focused on other proteases such as the cysteine cathepsins, particularly Cath-B, which has been shown to be up-regulated in a wide range of cancers [3]. However, as a result of close family homology, efforts to develop specific small molecule inhibitors towards cysteine cathepsins have been hindered by the inability to achieve selectivity [56]. Furthermore, side effects and toxicities may be further compounded by the accumulation of these inhibitors within the lysosomes (particularly in cathepsin-rich tissues such as the liver) [57]. The use of monoclonal antibodies in cancer therapy continues to gain in importance, due to the ability of these molecules to concentrate therapeutic effects onto neoplastic lesions while sparing normal organs [58-60]. Although originally monoclonal antibodies specific to membrane antigens on cancer cells have been used for tumor targeting applications, alternative targets such as markers of angiogenesis [61], stromal antigens [62], intracellular proteins released at sites of necrosis [63, 64], and proteases abnormally secreted are increasingly being considered. Inhibitory antibodies against the matrix metalloproteinases (MMPs) and the urokinase plasminogen activator uPA, were successfully obtained by phage display technology [51, 52]. More recently, antibody-mediated targeting of the cysteine Cath-S released in the tumor microenvironment was proposed as a potential therapeutic strategy [36, 65-68]. Alternately, the targeting of the uPA receptor with antagonistic human antibodies conjugated to the therapeutic radioisotope $^{177}$Lu was reported in aggressive breast cancer [69].

In this report, we propose that antibody-based targeting of Cath-D, which is up-regulated at the tumor site, may represent an additional attractive avenue for therapeutic applications in breast cancer. Given the potential pitfalls with small molecule inhibitors, the application of antibodies to antagonize Cath-D may offer significant therapeutic potential for cancer treatment. This approach allows the generation of a compound that is both specific towards Cath-D, and also will not accumulate in lysosomes, due to endosomal degradation. Furthermore, as the pathologic cath-D is secreted into the tumor microenvironment, it is therefore amendable to antibody compounds, as shown in this investigation. In conclusion, the use of an antibody that can selectively antagonize Cath-D in the tumor milieu may help circumvent toxicity issues that are likely to arise with small molecule inhibitors. The clinical utility of these initial findings with the anti-Cath-D antibody will need to be established through further investigations in preclinical models. We found that two human anti-Cath-D IgG1 crossreacted with murine Cath-D allowing further toxicity studies in syngenic mouse models. Since Cath-D may affect chemoresistance of BCC [70], it will be particularly important in the near future to combine the anti-cath-D human antibodies with existing chemotherapeutic agents for breast cancer.

REFERENCES

Throughout this application, various references describe the state of the art to which this invention pertains. The disclosures of these references are hereby incorporated by reference into the present disclosure.

1. Ono, M., et al., *A meta-analysis of cognitive impairment and decline associated with adjuvant chemotherapy in women with breast cancer.* Front Oncol, 2015. 5: p. 59.
2. Swartz, M. A., et al., *Tumor microenvironment complexity: emerging roles in cancer therapy.* Cancer Res, 2012. 72(10): p. 2473-80.
3. Turk, B., D. Turk, and V. Turk, *Protease signalling: the cutting edge.* EMBO J, 2012. 31(7): p. 1630-43.
4. Palermo, C. and J. A. Joyce, *Cysteine cathepsin proteases as pharmacological targets in cancer.* Trends Pharmacol Sci, 2008. 29(1): p. 22-8.
5. Cudic, M. and G. B. Fields, *Extracellular proteases as targets for drug development.* Curr Protein Pept Sci, 2009. 10(4): p. 297-307.
6. Reiser, J., B. Adair, and T. Reinheckel, *Specialized roles for cysteine cathepsins in health and disease.* J Clin Invest, 2010. 120(10): p. 3421-31.

7. Liaudet-Coopman, E., et al., *Cathepsin D: newly discovered functions of a long-standing aspartic protease in cancer and apoptosis*. Cancer Lett, 2006. 237(2): p. 167-79.
8. Ferrandina, G., et al., *Relationship between cathepsin-D content and disease-free survival in node-negative breast cancer patients: a meta-analysis*. Br J Cancer, 1997. 76(5): p. 661-6.
9. Foekens, J. A., et al., *Cathepsin-D in primary breast cancer: prognostic evaluation involving 2810 patients*. Br J Cancer, 1999. 79(2): p. 300-7.
10. Glondu, M., et al., *Down-regulation of cathepsin-D expression by antisense gene transfer inhibits tumor growth and experimental lung metastasis of human breast cancer cells*. Oncogene, 2002. 21(33): p. 5127-34.
11. Vetvicka, V., P. Benes, and M. Fusek, *Procathepsin D in breast cancer: what do we know? Effects of ribozymes and other inhibitors*. Cancer Gene Ther, 2002. 9(10): p. 854-63.
12. Garcia, M., et al., *Overexpression of transfected cathepsin D in transformed cells increases their malignant phenotype and metastasis potency*. Oncogene, 1990. 5(12): p. 1809-14.
13. Berchem, G., et al., *Cathepsin-D affects multiple tumor progression steps in vivo: proliferation, angiogenesis and apoptosis*. Oncogene, 2002. 21(38): p. 5951-5.
14. Glondu, M., et al., *A mutated cathepsin-D devoid of its catalytic activity stimulates the growth of cancer cells*. Oncogene, 2001. 20(47): p. 6920-9.
15. Hu, L., et al., *Thrombin up-regulates cathepsin D which enhances angiogenesis, growth, and metastasis*. Cancer Res, 2008. 68(12): p. 4666-73.
16. Laurent-Matha, V., et al., *Catalytically inactive human cathepsin D triggers fibroblast invasive growth*. J Cell Biol, 2005. 168(3): p. 489-99.
17. Vignon, F., et al., *Autocrine growth stimulation of the MCF 7 breast cancer cells by the estrogen-regulated 52 Kprotein*. Endocrinology, 1986. 118(4): p. 1537-45.
18. Fusek, M. and V. Vetvicka, *Mitogenic function of human procathepsin D: the role of the propeptide*. Biochem J, 1994. 303 (Pt 3): p. 775-80.
19. Roger, P., et al., *Cathepsin D immunostaining in paraffin-embedded breast cancer cells and macrophages: correlation with cytosolic assay*. Hum Pathol, 1994. 25(9): p. 863-71.
20. Erdmann, S., et al., *Inflammatory cytokines increase extracellular procathepsin D in permanent and primary endothelial cell cultures*. Eur J Cell Biol, 2008. 87(5): p. 311-23.
21. Behar, G., et al., *Isolation and characterization of anti-FcgammaRIII (CD16) llama single-domain antibodies that activate natural killer cells*. Protein Eng Des Sel, 2008. 21(1): p. 1-10.
22. Hasilik, A., et al., *Lysosomal enzyme precursors in human fibroblasts. Activation of cathepsin D precursor in vitro and activity of beta-hexosaminidase A precursor towards ganglioside GM2*. Eur J Biochem, 1982. 125(2): p. 317-21.
23. Griffiths, J. R., et al., *Why are cancers acidic? A carrier-mediated diffusion model for H+ transport in the interstitial fluid*. Novartis Found Symp, 2001. 240: p. 46-62; discussion 62-7, 152-3.
24. Stubbs, M., et al., *Causes and consequences of tumour acidity and implications for treatment*. Mol Med Today, 2000. 6(1): p. 15-9.
25. Schornack, P. A. and R. J. Gillies, *Contributions of cell metabolism and H+ diffusion to the acidic pH of tumors*. Neoplasia, 2003. 5(2): p. 135-45.
26. Laurent-Matha, V., et al., *Proteolysis of cystatin C by cathepsin D in the breast cancer microenvironment*. FASEB J, 2012.
27. Mason, S. D. and J. A. Joyce, *Proteolytic networks in cancer*. Trends Cell Biol, 2011. 21(4): p. 228-37.
28. Vetvicka, V., et al., *Analysis of the interaction of procathepsin D activation peptide with breast cancer cells*. Int J Cancer, 1997. 73(3): p. 403-9.
29. Beaujouin, M., et al., *Pro-cathepsin D interacts with the extracellular domain of the beta chain of LRP1 and promotes LRP1-dependent fibroblast outgrowth*. J Cell Sci, 2010. 123(Pt 19): p. 3336-46.
30. Derocq, D., et al., *Cathepsin D is partly endocytosed by the LRP1 receptor and inhibits LRP1-regulated intramembrane proteolysis*. Oncogene, 2012. 31(26): p. 3202-12.
31. Elkon, K. and P. Casali, *Nature and functions of autoantibodies*. Nat Clin Pract Rheumatol, 2008. 4(9): p. 491-8.
32. Piura, E. and B. Piura, *Autoantibodies to tumor-associated antigens in breast carcinoma*. J Oncol, 2010. 2010: p. 264926.
33. Taylor, D. D., C. Gercel-Taylor, and L. P. Parker, *Patient-derived tumor-reactive antibodies as diagnostic markers for ovarian cancer*. Gynecol Oncol, 2009. 115(1): p. 112-20.
34. Liu, Y., et al., *Serum autoantibody profiling using a natural glycoprotein microarray for the prognosis of early melanoma*. J Proteome Res, 2010. 9(11): p. 6044-51.
35. Luo, X., et al., *Comparative autoantibody profiling before and after appearance of malignance: identification of anti-cathepsin D autoantibody as a promising diagnostic marker for lung cancer*. Biochem Biophys Res Commun, 2012. 420(4): p. 704-9.
36. Burden, R. E., et al., *Antibody-mediated inhibition of cathepsin S blocks colorectal tumor invasion and angiogenesis*. Clin Cancer Res, 2009. 15(19): p. 6042-51.
37. Philibert, P., et al., *A focused antibody library for selecting scFvs expressed at high levels in the cytoplasm*. BMC Biotechnol, 2007. 7: p. 81.
38. Robin, G. and P. Martineau, *Synthetic customized scFv libraries*. Methods Mol Biol, 2012. 907: p. 109-22.
39. Baldwin, E. T., et al., *Crystal structures of native and inhibited forms of human cathepsin D: implications for lysosomal targeting and drug design*. Proc Natl Acad Sci USA, 1993. 90(14): p. 6796-800.
40. Gradler, U., et al., *Structure-based optimization of non-peptidic Cathepsin D inhibitors*. Bioorg Med Chem Lett, 2014. 24(17): p. 4141-50.
41. Lee, A. Y., S. V. Gulnik, and J. W. Erickson, *Conformational switching in an aspartic proteinase*. Nat Struct Biol, 1998. 5(10): p. 866-71.
42. Saftig, P., et al., *Mice deficient for the lysosomal proteinase cathepsin D exhibit progressive atrophy of the intestinal mucosa and profound destruction of lymphoid cells*. Embo J, 1995. 14(15): p. 3599-608.
43. Siintola, E., et al., *Cathepsin D deficiency underlies congenital human neuronal ceroid-lipofuscinosis*. Brain, 2006. 129(Pt 6): p. 1438-45.
44. Wu, Y., et al., *Structural insight into distinct mechanisms of protease inhibition by antibodies*. Proc Natl Acad Sci USA, 2007. 104(50): p. 19784-9.

45. Garcia, M., et al., *Characterization of monoclonal antibodies to the estrogen-regulated Mr 52,000 glycoprotein and their use in MCF7 cells.* Cancer Res, 1985. 45(2): p. 709-16.
46. Freiss, G., F. Vignon, and H. Rochefort, *Characterization and properties of two monoclonal antibodies specific for the Mr 52,000 precursor of cathepsin D in human breast cancer cells.* Cancer Res, 1988. 48(13): p. 3709-15.
47. Freiss, G., et al., *A two-site immunoenzymometric assay of 52-kDa pro-cathepsin D, and its use in human breast diseases.* Clin Chem, 1989. 35(2): p. 234-7.
48. Rogier, H., et al., *Two-site immunoenzymometric assay for the 52-kDa cathepsin D in cytosols of breast cancer tissues.* Clin Chem, 1989. 35(1): p. 81-5.
49. Vetvicka, V., J. Vetvickova, and M. Fusek, *Anti-human procathepsin D activation peptide antibodies inhibit breast cancer development.* Breast Cancer Res Treat, 1999. 57(3): p. 261-9.
50. Winter, G., et al., *Making antibodies by phage display technology.* Annu Rev Immunol, 1994. 12: p. 433-55.
51. Pfaffen, S., et al., *Isolation and characterization of human monoclonal antibodies specific to MMP-1A, MMP-2 and MMP-3.* Exp Cell Res, 2010. 316(5): p. 836-47.
52. Sgier, D., et al., *Isolation and characterization of an inhibitory human monoclonal antibody specific to the urokinase-type plasminogen activator, uPA.* Protein Eng Des Sel, 2010. 23(4): p. 261-9.
53. Nimmerjahn, F. and J. V. Ravetch, *Translating basic mechanisms of IgG effector activity into next generation cancer therapies.* Cancer Immun, 2012. 12: p. 13.
54. Overall, C. M. and C. Lopez-Otin, *Strategies for MMP inhibition in cancer: innovations for the post-trial era.* Nat Rev Cancer, 2002. 2(9): p. 657-72.
55. Coussens, L. M., B. Fingleton, and L. M. Matrisian, *Matrix metalloproteinase inhibitors and cancer: trials and tribulations.* Science, 2002. 295(5564): p. 2387-92.
56. Turk, B., *Targeting proteases: successes, failures and future prospects.* Nat Rev Drug Discov, 2006. 5(9): p. 785-99.
57. Black, W. C. and M. D. Percival, *The consequences of lysosomotropism on the design of selective cathepsin K inhibitors.* Chembiochem, 2006. 7(10): p. 1525-35.
58. Carter, P. J., *Potent antibody therapeutics by design.* Nat Rev Immunol, 2006. 6(5): p. 343-57.
59. Schrama, D., R. A. Reisfeld, and J. C. Becker, *Antibody targeted drugs as cancer therapeutics.* Nat Rev Drug Discov, 2006. 5(2): p. 147-59.
60. Weiner, L. M., *Fully human therapeutic monoclonal antibodies.* J Immunother, 2006. 29(1): p. 1-9.
61. Neri, D. and R. Bicknell, *Tumour vascular targeting.* Nat Rev Cancer, 2005. 5(6): p. 436-46.
62. Hofheinz, R. D., et al., *Stromal antigen targeting by a humanised monoclonal antibody: an early phase II trial of sibrotuzumab in patients with metastatic colorectal cancer.* Onkologie, 2003. 26(1): p. 44-8.
63. Miller, G. K., et al., *Immunologic and biochemical analysis of TNT-1 and TNT-2 monoclonal antibody binding to histones.* Hybridoma, 1993. 12(6): p. 689-98.
64. Street, H. H., et al., *Phase I study of 131I-chimeric(ch) TNT-1/B monoclonal antibody for the treatment of advanced colon cancer.* Cancer Biother Radiopharm, 2006. 21(3): p. 243-56.
65. Kwok, H. F., et al., *Antibody targeting of Cathepsin S induces antibody-dependent cellular cytotoxicity.* Mol Cancer, 2011. 10: p. 147.
66. Burden, R. E., et al., *Inhibition of Cathepsin S by Fsn0503 enhances the efficacy of chemotherapy in colorectal carcinomas.* Biochimie, 2012. 94(2): p. 487-93.
67. Vazquez, R., et al., *FsnO503h antibody-mediated blockade of cathepsin S as a potential therapeutic strategy for the treatment of solid tumors.* Biochimie, 2015. 108: p. 101-7.
68. Wilkinson, R. D., et al., *Cathepsin S: therapeutic, diagnostic and prognostic potential.* Biol Chem, 2015.
69. LeBeau, A. M., et al., *Targeting uPAR with antagonistic recombinant human antibodies in aggressive breast cancer.* Cancer Res, 2013. 73(7): p. 2070-81.
70. Vetvicka, V., M. Fusek, and A. Vashishta, *Procathepsin d involvement in chemoresistance of cancer cells.* N Am J Med Sci, 2012. 4(4): p. 174-9.
71. Laurent-Matha, V., et al., *Processing of human cathepsin D is independent of its catalytic function and autoactivation: involvement of cathepsins L and B.* J Biochem, 2006. 139(3): p. 363-71.
72. Faust, P. L., S. Kornfeld, and J. M. Chirgwin, *Cloning and sequence analysis of cDNA for human cathepsin D.* Proc Natl Acad Sci USA, 1985. 82(15): p. 4910-4.
73. Lefranc, M. P., et al., *IMGT unique numbering for immunoglobulin and T cell receptor variable domains and Ig superfamily V-like domains.* Dev Comp Immunol, 2003. 27(1): p. 55-77.

The invention claimed is:

1. An isolated human anti-Cath-D monoclonal antibody or antigen binding fragment thereof, wherein the antibody or antigen binding fragment thereof inhibits both Cath-D catalytic activity and Cath-D binding to an LRP1 receptor and comprises a heavy chain variable region comprising SEQ ID NO: 2 in the H-CDR1 region, SEQ ID NO: 3 in the H-CDR2 region and SEQ ID NO: 4 in the H-CDR3 region, and a light chain variable region comprising SEQ ID NO: 6 in the L-CDR1 region, SEQ ID NO: 7 in the L-CDR2 region and SEQ ID NO: 8 in the L-CDR3 region.

2. The antibody according to claim 1, wherein the heavy chain variable region has the amino acid sequence set forth as SEQ ID NO: 1.

3. The antibody according to claim 1, wherein the light chain variable region has the amino acid sequence set forth as SEQ ID NO: 5.

4. The antibody according to claim 1, wherein the heavy chain variable region has the amino acid sequence set forth as SEQ ID NO: 1 and the light chain variable region has the amino acid sequence set forth as SEQ ID NO: 5.

5. An isolated human anti-Cath-D monoclonal antibody or antigen binding fragment thereof, wherein the antibody or antigen binding fragment thereof inhibits both Cath-D catalytic activity and Cath-D binding to an LRP1 receptor and comprises a heavy chain variable region comprising SEQ ID NO: 10 in the H-CDR1 region, SEQ ID NO: 11 in the H-CDR2 region and SEQ ID NO: 12 in the H-CDR3 region, and a light chain variable region comprising SEQ ID NO: 14 in the L-CDR1 region, SEQ ID NO: 15 in the L-CDR2 region and SEQ ID NO: 16 in the L-CDR3 region.

6. The antibody according to claim 5, wherein the heavy chain variable region has the amino acid sequence set forth as SEQ ID NO: 9.

7. The antibody according to claim 5, wherein the light chain variable region has the amino acid sequence set forth as SEQ ID NO: 13.

8. The antibody according to claim 5, wherein the heavy chain variable region has the amino acid sequence set forth as SEQ ID NO: 9 and the light chain variable region has the amino acid sequence set forth as SEQ ID NO: 13.

9. An isolated nucleic acid sequence encoding the heavy chain variable region according to claim 2.

10. An isolated vector comprising the nucleic acid sequence according to claim 9.

11. A host cell comprising the vector according to claim 10.

12. An isolated nucleic acid sequence encoding the light chain variable region according to claim 3.

13. An isolated vector comprising the nucleic acid sequence according to claim 12.

14. A host cell comprising the vector according to claim 13.

15. A pharmaceutical composition comprising the antibody or antigen binding fragment thereof according to claim 1.

16. A method for treating breast cancer comprising administering to a patient in need thereof a therapeutically effective amount of the isolated human anti-Cath-D monoclonal antibody or antigen binding fragment thereof according to claim 1.

* * * * *